(12) United States Patent
White et al.

(10) Patent No.: US 10,603,452 B2
(45) Date of Patent: Mar. 31, 2020

(54) METHOD AND APPARATUS FOR THE CONTROLLED DELIVERY OF GASES

(71) Applicant: AUCKLAND UNIVERSITY OF TECHNOLOGY, Auckland (NZ)

(72) Inventors: David Edward White, Auckland (NZ); James Russell Frederick Bartley, Auckland (NZ); Jonathan David Currie, Auckland (NZ); Ian Douglas Makinson, Auckland (NZ); Alastair Edwin McAuley, Rotorua (NZ); Roy Jonathan Nates, Auckland (NZ)

(73) Assignee: AUCKLAND UNIVERSITY OF TECHNOLOGY, Auckland (NZ)

( * ) Notice: Subject to any disclaimer, the term of this patent is extended or adjusted under 35 U.S.C. 154(b) by 0 days.

(21) Appl. No.: 15/516,668

(22) PCT Filed: Oct. 5, 2015

(86) PCT No.: PCT/NZ2015/050169
§ 371 (c)(1),
(2) Date: Apr. 3, 2017

(87) PCT Pub. No.: WO2016/053119
PCT Pub. Date: Apr. 7, 2016

(65) Prior Publication Data
US 2017/0296767 A1     Oct. 19, 2017

(30) Foreign Application Priority Data

Oct. 3, 2014   (NZ) ........................ 700670

(51) Int. Cl.
*A61M 16/00*     (2006.01)
*A61M 16/20*     (2006.01)
(Continued)

(52) U.S. Cl.
CPC .... *A61M 16/0066* (2013.01); *A61M 16/0069* (2014.02); *A61M 16/024* (2017.08);
(Continued)

(58) Field of Classification Search
CPC .............. A61M 15/00; A61M 15/0001; A61M 15/002; A61M 15/0013;
(Continued)

(56) References Cited

U.S. PATENT DOCUMENTS

| 7,114,497 B2 | 10/2006 | Aylsworth et al. |
| 2004/0173210 A1 | 9/2004 | Campbell |

(Continued)

FOREIGN PATENT DOCUMENTS

| WO | 2003082393 A1 | 10/2003 |
| WO | 2005009501 A1 | 2/2005 |

(Continued)

OTHER PUBLICATIONS

Foreign Communication from a Related Counterpart Application, International Search Report and Written Opinion dated Dec. 10, 2015, International Application No. PCT/NZ2015/050169 filed on Oct. 5, 2015.

(Continued)

*Primary Examiner* — Samchuan C Yao
*Assistant Examiner* — Ned T Heffner

(57) ABSTRACT

A method of controlled delivery of breathing gases is described the method comprising: applying breathing gas pressure within the first naris of a patient during inhalation; applying breathing gas pressure within the second naris of the patient during inhalation; applying breathing gas pressure within the first naris of the patient during exhalation; and applying breathing gas pressure within the second naris of the patient during exhalation, wherein the breathing gas pressure applied to the first naris during inhalation is higher (Continued)

than the gas pressure applied to the second naris during inhalation and the breathing gas inflow to the patient is substantially through the first naris during inhalation and wherein the breathing gas pressure applied to the first naris during exhalation is lower than the gas pressure applied to the second naris during exhalation and the gas outflow from the patient is substantially through the first naris during exhalation. An apparatus and system implementing the method is also described.

25 Claims, 17 Drawing Sheets

(51) Int. Cl.
  *A61M 16/06* (2006.01)
  *A61M 16/10* (2006.01)
(52) U.S. Cl.
  CPC .... *A61M 16/0616* (2014.02); *A61M 16/1005* (2014.02); *A61M 16/204* (2014.02); *A61M 16/209* (2014.02); *A61M 2016/0027* (2013.01); *A61M 2016/0036* (2013.01); *A61M 2202/0208* (2013.01); *A61M 2205/3334* (2013.01); *A61M 2205/3344* (2013.01); *A61M 2205/3375* (2013.01); *A61M 2210/0618* (2013.01); *A61M 2230/04* (2013.01); *A61M 2230/10* (2013.01); *A61M 2230/14* (2013.01); *A61M 2230/46* (2013.01); *A61M 2230/62* (2013.01); *A61M 2230/63* (2013.01)

(58) Field of Classification Search
  CPC . A61M 2230/40–46; A61M 2016/0015–0042; A61M 16/00; A61M 16/06; A61M 16/0666–0694; A61M 16/10; A61M 16/104; A61M 16/1005; A61M 16/12; A61M 16/122; A61M 16/125; A61M 16/127
  See application file for complete search history.

(56) References Cited

U.S. PATENT DOCUMENTS

| | | | |
|---|---|---|---|
| 2005/0011523 A1* | 1/2005 | Aylsworth | A61M 16/00 128/207.18 |
| 2006/0174885 A1* | 8/2006 | Aylsworth | A61M 16/10 128/206.11 |
| 2006/0272643 A1 | 12/2006 | Aylsworth | |
| 2007/0272239 A1 | 11/2007 | Aylsworth | |
| 2007/0272240 A1 | 11/2007 | Aylsworth | |
| 2015/0020810 A1 | 1/2015 | Stupak | |

FOREIGN PATENT DOCUMENTS

| | | |
|---|---|---|
| WO | 2005009501 A2 | 2/2005 |
| WO | 2006086190 A2 | 8/2006 |
| WO | 2008014543 A1 | 2/2008 |
| WO | 2008077003 A1 | 6/2008 |
| WO | 2009094532 A1 | 7/2009 |
| WO | 2009132753 A1 | 11/2009 |
| WO | 2009146484 A1 | 12/2009 |
| WO | 2010076711 A1 | 7/2010 |
| WO | 2011022779 A1 | 3/2011 |
| WO | 2011141841 A1 | 11/2011 |
| WO | 2012134810 A2 | 10/2012 |
| WO | 2013009376 A1 | 1/2013 |
| WO | 2014085431 A1 | 6/2014 |
| WO | 2014091362 A1 | 6/2014 |
| WO | 2015020540 A1 | 2/2015 |
| WO | 2016053119 A1 | 4/2016 |

OTHER PUBLICATIONS

Foreign Communication from a Related Counterpart Application, Australian Examination Report dated Sep. 21, 2017, Australian Application No. 2015324693, filed Oct. 3, 2014.
Foreign Communication from a Related Counterpart Application, European Examination Report dated Apr. 16, 2018, European Application No. 15846809.0.
Foreign Communication from a Related Counterpart Application, New Zealand First Examination Report dated Oct. 17, 2017, NZ Application No. 731209.
Foreign Communication from a Related Counterpart Application, New Zealand Further Examination Report dated May 10, 2018, NZ Application No. 731209.
Hanif, J., S.S.M. Jawad, and R. Eccles, The nasal cycle in health and disease. Clinical Otolaryngology, 2000. 25(6): p. 461-467.
Bartley, J., Breathing Matters: a New Zealand Guide. 1st. ed. 2006, Auckland: Random House. 219.
Elad, D., M. Wolf, and T. Keck, Air-conditioning in the human nasal cavity. Respiratory Physiology and Neurobiology, 2008. 163(1-3): p. 121-127.
Naftali, S., et al., The air-conditioning capacity of the human nose. Ann Biomed Eng, 2005. 33(4): p. 545-553.
Chhabra, N. and S.M. Houser, The Diagnosis and Management of Empty Nose Syndrome. Otolaryngologic Clinics of North America, 2009. 42(2): p. 311-330.
Drettner, B., B. Falck, and H. Simon, Measurements of the Air Conditioning Capacity of the Nose During Normal and Pathological Conditions and Pharmacological Influence. Acta Oto-Laryngologica, 1977. 84(1-6): p. 266-277.
Keck, T., et al., Humidity and temperature profile in the nasal cavity. Rhinology, 2000. 38(4): p. 167-171.
Cole, P., Modification of Inspired Air, in The Nose: Upper Airway Physiology and the Atmospheric Environment., D.F. Proctor and I. Andersen, Editors. 1982, Elsevier Biomedical Press: Amsterdam. p. 351-375.
Wolf, M., et al., Air-conditioning characteristics of the human nose. Journal of Laryngology and Otology, 2004. 118(2): p. 87-92.
Warren, N., E. Crampin, and M. Tawhai, The Role of Airway Epithelium in Replenishment of Evaporated Airway Surface Liquid From the Human Conducting Airways. Annals of Biomedical Engineering, 2010. 38(12): p. 3535-3549.
Eccles, R., Neurological and pharmacological considerations, in The nose: upper airway physiology and the atmospheric environment., D.F. Proctor and I. Andersen, Editors. 1982, Elsevier Biomedical Press: Amsterdam. p. 191-214.
White, D.E., J. Bartley, and R. Nates, Model demonstrates functional purpose of the nasal cycle. Biomedical Engineering Online, 2015. 14(38): p. 11.
Jella, S.A. and D.S. Shannahoff-khalsa, The effects of unilateral forced nostril breathing on cognitive performance. International Journal of Neuroscience, 1993. 73(1-2): p. 61-68.
Shannahoff-khalsa, D.S., M.R. Boyle, and M.E. Buebel, The Effects of Unilateral Forced Nostril Breathing on Cognition. International Journal of Neuroscience, 1991. 57(3-4): p. 239-249.
Shannahoff-Khalsa, D.S., et al., Ultradian rhythms of alternating cerebral hemispheric EEG dominance are coupled to rapid eye movement and non-rapid eye movement stage 4 sleep in humans. Sleep Medicine, 2001. 2(4): p. 333-346.
Shannahoff-khalsa, D.S. and F.E. Yates, Ultradian Sleep Rhythms of Lateral EEG, Autonomic, and Cardiovascular Activity Are Coupled in Humans. International Journal of Neuroscience, 2000. 101(1-4): p. 21-43.
Shannahoff-Khalsa, D.S., et al., Low-frequency ultradian insulin rhythms are coupled to cardiovascular, autonomic, and neuroendocrine rhythms. American Journal of Physiology—Regulatory, Integrative and Comparative Physiology, 1997. 272(3): p. R962-R968.
Martins de Araujo, M.T., et al., Heated humidification or face mask to prevent upper airway dryness during continuous positive airway pressure therapy. Chest, 2000. 117: p. 142-147.

(56) References Cited

OTHER PUBLICATIONS

Massie, C.A., et al., Effects of humidification on nasal symptoms and compliance in sleep apnea patients using continuous positive airway pressure. Chest, 1999. 116: p. 403-408.
Neill, A.M., et al., Humidified nasal continuous positive airway pressure in obstructive sleep apnoea. European Respiratory Journal, 2003. 22(2): p. 258-262.
Rakotonanahary, D., et al., Predictive factors for the need for additional humidification during nasal continuous positive airway pressure therapy. Chest, 2001. 119(2): p. 460-465.
Wiest, G.H., et al., A heated humidifier reduces upper airway dryness during continuous positive airway pressure therapy. Respiratory Medicine, 1999. 93(1): p. 21-26.
Worsnop, C.J., S. Miseski, and P.D. Rochford The routine use of humidification with nasal continuous positive airway pressure. Internal Medicine Journal, 2009. 99, DOI: 10.1111/j.1445-5994.2009.01969.x.
Dolan, D.C., et al., Longitudinal comparison study of pressure relief (C-Flex(TM)) vs. CPAP in OSA patients. Sleep and Breathing, 2009. 13(1): p. 73-7.
Arfoosh, R. and J. Rowley, Continuous positive airway pressure for obstructive sleep apnea: an update. Journal of Respiratory Diseases, 2008. 29(9): p. 365-373.
Mador, M.J., et al., Effect of heated humidification on compliance and quality of life in patients with sleep apnea using nasal continuous positive airway pressure. Chest, 2005. 128(4): p. 2151-2158.
Goldstein, L., N.W. Stoltzfus, and J.F. Gardocki, Changes in interhemispheric amplitude relationships in the EEG during sleep. Physiology & Behavior, 1972. 8(5): p. 811-815.
Kimura, A., et al., Phase of nasal cycle during sleep tends to be associated with sleep stage. The Laryngoscope, 2013.

\* cited by examiner

METHOD AND APPARATUS FOR THE CONTROLLED DELIVERY OF GASES

CROSS-REFERENCE TO RELATED APPLICATIONS

The present application is a filing under 35 U.S.C. 371 as the National Stage of International Application No. PCT/NZ2015/050169, filed Oct. 5, 2015, entitled "A METHOD AND APPARATUS FOR THE CONTROLLED DELIVERY OF GASES," which claims priority to New Zealand Application No. 700670 filed with the Intellectual Property Office of New Zealand on Oct. 3, 2014, both of which are incorporated herein by reference in their entirety for all purposes.

FIELD OF INVENTION

The present invention relates to a method and apparatus for the controlled delivery of gases. In particular to the invention relates to a method and apparatus for the controlled delivery of gases were the bias of inter-nasal airflow is towards one side.

BACKGROUND TO THE INVENTION

The disclosure in the applicants New Zealand Provisional Application Number NZ700670 A Method and Apparatus for the Controlled Delivery of Gases, White et al, is expressly incorporated herein by reference.

Putting aside the role of olfaction, the primary function of the nose is to heat and humidify inhaled air as well as trap and remove debris and pathogens. Heat and humidification are provided by blood flow and airway surface liquid (ASL) respectively. The upper mucus layer within the ASL provides a means of entrapping inhaled debris and pathogens which are then transported by the mucociliary transport towards the nasopharynx for disposal by swallowing or expectoration.

All mammals, including man, have two nasal passageways which typically carry a differing apportionment of tidal airflow. Periodic change in inter-nasal airflow apportionment is known as the nasal cycle. In healthy humans, the nose is the preferred entry point for air entering the airways, serving an important role in maintaining airway health by entrapping inhaled pathogens and pollutants as well as heating and humidifying inhaled air. During nasal breathing, the nose recovers around 30% of exhaled heat and water vapour and provides a region for olfaction to occur. The entire conducting airway is lined with an airway surface liquid (ASL) that not only provides the means of entrapment of inhaled pathogens and pollutants, but is also the medium through which heat and water must pass though from the underlying mucosa. While the nasal airways in all healthy mammals, including man, demonstrate the nasal cycle, the physiological reason for this phenomenon has previously not been well understood. Early work by Eccles et al. (1982) proposed that the 'nasal cycle' enables cells and glands to rest and recharge. Later work has hinted that the 'nasal cycle is probably controlling the balance between the fluxes of heat and water vapour required to condition the inspired air and the ability of nasal blood flow and mucus secretion to supply sufficient heat and water to the surface tissue surface.

More recent work has demonstrated that the nasal cycle provides a means by which the anterior conducting airway copes with conflicting ASL hydration states where each passageway alternatively take turns in either predominantly undertaking the air-conditioning with resultant airway drying or a mucus clearance role where the airway surface liquid remains hydrated. Each of these roles requires different airflow conditions, which are provided by differing rates of airflow passing down each airway.

Apart from its functional role in maintaining airway health, change in the nasal cycle phase in the awake state has also been linked to variation in human cognitive performance on verbal and spatial tasks and cognition associated with alternation of cerebral dominance. During sleep, nasal cycle phase has been linked to ultradian sleep rhythms and autonomic and cardiovascular activities. This work has suggested nasal breathing influences brain activity laterality, brain and body blood flows, heart rate and stroke volume, blood pressure, as well as hormone production.

Normally both nasal airways cycle between two airflow states with one passageway experiencing a higher airflow than the other. This cycle is achieved by varying the passageway geometry through activation of mucosal blood capacitance vessels. The un-obstructed airway, termed 'patent', passes the majority of the airflow while the other 'congested' airway passes a much lower amount. This bias of inter-nasal airflow toward the 'patent' side enables the congested airway to maintain a sufficient ASL hydration level so that effective mucociliary transport can occur. It also allows cells and glands on this side to rest and recharge as there is little fluid demand from the ASL to humidify inhaled air on this side.

The patent side however carries the bulk of the heating and humidification duty and in doing so experiences ASL dehydration and subsequent re-wetting during inhalation and exhalation breath phases respectively. This cyclic ASL dehydration/re-wetting not only exposes the mucosa of this airway to repeated drying and high cellular/gland fluid demands, it also disables the mucociliary transport system within this airway. Different airflow rates within each airway channel are achieved by each airway having either a high or low resistance to tidal airflow. This enables the nose to effectively undertake all if its functions despite the contrasting airflow requirements between air-conditioning and filtration of inhaled air. Typically this bias in airflow between nasal airways lasts for a period of time before swapping sides in what is termed 'the nasal cycle'. The purpose of this cycle is to enable each airway to take its turn in either being 'congested' or 'patent' through a switch in the nasal cycle.

Normal inter-nasal airflow partitioning is disturbed during nasal breathing of pressurised air or other gases. The disturbance is characterised by the previously 'patent' airway becoming more restrictive to airflow while the previously 'congested airway' becomes less restrictive. This change disrupts the normal functioning of the nasal cycle by altering the normal inter-nasal airflow partitioning ratio between the two airways. Pressure elicited change in nasal geometry causes a reduction in the apportionment of tidal airflow through the previously 'patent airway' and a greater apportionment to occur through the 'previously congested' airway. This leads to cyclic ASL drying to occur along both nasal airways during inhalation which disables mucociliary transport and cellular/gland rest and recovery within the nose.

Nasal breathing of pressurised air or other gases, during treatments such as continuous positive air pressure (CPAP), bi-level air positive air pressure (Bi-PAP) and auto-titrating positive air pressure (APAP), are used to treat obstructive sleep apnoea (OSA). Users of this treatment frequently report symptoms associated with airway drying. This occurs as a consequence of the pressure elicited change in airflow partitioning which prevents the previously 'patent airway' from experiencing sufficient re-hydration from condensing outflowing air. Mucosal drying can also occur in the previously 'congested airway' as it is now forced to conduct a greater airflow during a period where it would normally experience rest and recovery. Re-wetting through condensing exhaled air can occur in just a couple of exhalation breaths that may take approximately 10 seconds. Supplementary humidification is frequently used to relieve these symptoms but does not seem to lead to improved adherence to the breathing therapy, suggesting that the cause of patient dissatisfaction might be more complex than simply a case of airway drying.

Another significant but mostly overlooked factor concerns the neurological interaction occurring between the nose and hypothalamus. The ultradian rhythm regulated by the hypothalamus regulates many aspects of the central and autonomic nervous systems as well as the regulation of hormones and other active or signalling agents. This regulation includes the basic rest-activity cycle (BRAC) and sleep rhythms through regulation. Human performance, cognition and cerebral hemispheric activity have all been found to be influenced by nasal airflow asymmetries. Forced change in the bias of inter-nasal airflow that normally occurs between the 'patent' and 'congested' airways can be achieved through the blocking of one airway during nasal breathing of ambient air. This disturbance in normal nasal breathing has been found to influence the hypothalamus through change in ultradian rhythms and BRAC cycle.

WO2011141841 describes a system to deliver the pressurized flow of breathable gas to only a first nostril of the subject such that the airway of the subject is pressurized by the pressurized flow of breathable gas through the first nostril.

U.S. Pat. No. 7,114,497 describes a method and system of individually controlling positive airway pressure of a patient's nares.

It is an object of the present invention to actively regulate inter-nasal airflow partitioning during pressurised or ambient nasal breathing to replicate normal inter-nasal airflow partitioning found during ambient pressure breathing.

It is a further object of the present invention to actively regulate the switch of the inter-nasal airflow apportionment occurring between each of the nasal airways and in doing so mimic the change in status of inter-nasal airflow partitioning that occurs during the nasal cycle.

A further object of the present invention is to influence the neurological interactions between brain and nasal airways and thereby alter the regulation of the body's autonomic and sympathetic nervous systems. This airway/brain interaction influences many ultradian cycle activities, including hormone release and the Basic Rest Activity Cycle (BRAC).

It is a further object of the invention to provide a method and apparatus for providing a flow of pressurised gases which goes some way towards overcoming the abovementioned disadvantages or which at least provides the public or industry with a useful choice.

Further objects and advantages of the invention will be brought out in the following portions of the specification, wherein the detailed description is for the purpose of fully disclosing the preferred embodiment of the invention without placing limitations thereon.

The background discussion (including any potential prior art) is not to be taken as an admission of the common general knowledge.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e. they will be taken to mean an inclusion of the listed components which the use directly references, and possibly also of other non-specified components or elements.

SUMMARY OF INVENTION

In one aspect, the invention may broadly be said to consist in a method of controlled delivery of breathing gases, comprising:

applying breathing gas pressure within the first naris of a patient during inhalation;

applying breathing gas pressure within the second naris of the patient during inhalation;

applying breathing gas pressure within the first naris of the patient during exhalation; and applying breathing gas pressure within the second naris of the patient during exhalation, wherein the breathing gas pressure applied to the first naris during inhalation is higher than the gas pressure applied to the second naris during inhalation and the breathing gas inflow to the patient is substantially through the first naris during inhalation and wherein the breathing gas pressure applied to the first naris during exhalation is lower than the gas pressure applied to the second naris during exhalation and the gas outflow from the patient is substantially through the first naris during exhalation.

Preferably the method forces the breathing gases inflow and outflow through the first naris.

Preferably pressures are switched to control the breathing gas inflow and outflow substantially through the second naris after a period of time greater than one breath cycle.

Preferably the change in the pressures applied to the first and second naris is driven by a predetermined period that is user programmable.

Preferably the predetermined period is 5 minutes to 360 minutes.

Preferably the breathing gas pressure is applied to each naris through a substantially sealed mask.

Alternatively the breathing gas pressure is applied to each naris through an unsealed mask or open cannula.

Preferably the pressure differences between each nares are greater at the midpoint of the inhalation and exhalation phases than they are at the start and end of each phase.

Preferably the largest pressure differences between each nares are applied when net patient air flow, in or out, is above a certain threshold.

Preferably the pressure differences are the smallest during the start and end of the inhalation and exhalation phases.

Preferably the pressure delivered to one naris always achieves the maximal titration pressure during peak airflow for either inhalation or exhalation phases.

Preferably the lower pressure is progressively elevated to the maximal titration pressure pressures commencing at the start and end of the inhalation and start and end of the exhalation phase.

Preferably the lower pressure is progressively elevated to the higher pressure when at least one of the flow rates is below a certain threshold.

Preferably the lower pressure is progressively elevated to the higher pressure, when the rate of change of at least one of the flow rates is below a certain threshold.

Preferably pressures delivered to each nares are progressively closer to each other at the start and end of the inhalation and start and end of the exhalation phase.

Preferably pressures are closer to each other when at least one of the flow rates is below a certain threshold.

Preferably the maximal titration pressure is a continuous set value.

Alternatively the maximal titration pressure is a pre-set bi-level value.

Alternatively the maximal titration pressure is varied based on measured airflow.

Alternatively the maximal titration pressure is set by a pre-determined pressure relief function.

Preferably the method is used for treating snoring or obstructive sleep apnoea.

Preferably the method is used for oxygen therapy.

In a second aspect, the invention may broadly be said to consist in a method of controlled delivery of breathing gases, comprising:
 applying breathing gas pressure within the first naris of a patient during inhalation;
 applying breathing gas pressure within the second naris of the patient during inhalation;
 applying breathing gas pressure within the first naris of the patient during exhalation; and
 applying breathing gas pressure within the second naris of the patient during exhalation,
 wherein the breathing gas pressure applied to the first naris during inhalation and exhalation is higher than the gas pressure applied to the second naris such that the breathing gas inflow to the patient is substantially through the first naris during inhalation and the breathing gas outflow is substantially through the second naris during exhalation.

Preferably the method forces the breathing gases inflow through the first naris and outflow through the second naris.

Preferably pressures are switched such that the breathing gas inflow to the patient is substantially through the second naris during inhalation and the breathing gas outflow is substantially through the first naris during exhalation after a period of time greater than one breath cycle.

Preferably the change in the pressures applied to the first and second naris is driven by a predetermined period that is user programmable.

Preferably the predetermined period is 5 minutes to 360 minutes.

Preferably the breathing gas pressure is applied to each naris through a substantially sealed mask.

Preferably the breathing gas pressure is applied to each naris through an unsealed mask or open cannula.

Preferably the pressure differences between each nares are greater at the midpoint of the inhalation and exhalation phases than they are at the start and end of each phase.

Preferably the largest pressure differences between each nares are applied when net patient air flow, in or out, is above a certain threshold.

Preferably the pressure differences are the smallest during the start and end of the inhalation and exhalation phases.

Preferably the pressure delivered to one naris always achieves the maximal titration pressure during peak airflow for either inhalation or exhalation phases.

Preferably the lower pressure is progressively elevated to the maximal titration pressure pressures commencing at the start and end of the inhalation and start and end of the exhalation phase.

Preferably the lower pressure is progressively elevated to the higher pressure when at least one of the flow rates is below a certain threshold.

Preferably the lower pressure is progressively elevated to the higher pressure, when the rate of change of at least one of the flow rates is below a certain threshold.

Preferably pressures delivered to each nares are progressively closer to each other at the start and end of the inhalation and start and end of the exhalation phase.

Preferably pressures are closer to each other when at least one of the flow rates is below a certain threshold.

Preferably the maximal titration pressure is a continuous set value.

Alternatively the maximal titration pressure is a pre-set bi-level value.

Alternatively the maximal titration pressure is varied based on measured airflow.

Alternatively the maximal titration pressure is set by a pre-determined pressure relief function.

Preferably the method is used for treating snoring or obstructive sleep apnoea.

Preferably the method is used for oxygen therapy.

In a third aspect, the invention may broadly be said to consist in an apparatus for the controlled delivery of breathing gases to a patient, comprising:
 a fluid connection between a gases flow generator to each of a first and second naris of the patent; and
 a controller for controlling the pressure of the gases supplied to the first and second naris of the patent, the controller configured to:
 apply breathing gas pressure within the first naris of a patient during inhalation;
 apply breathing gas pressure within the second naris of the patient during inhalation;
 apply breathing gas pressure within the first naris of the patient during exhalation; and
 apply breathing gas pressure within the second naris of the patient during exhalation, wherein the breathing gas pressure applied to the first naris is higher than the breathing gas pressure applied to the second naris during inhalation such that the breathing gas inflow to the patient is substantially through the first naris and wherein the breathing gas pressure applied to the first naris is lower than the breathing gas pressure applied to the second naris during exhalation such that the gas outflow from the patient is substantially through the first naris.

Preferably the controller forces the breathing gases inflow and outflow through the first naris.

Preferably the apparatus further comprises a flow control valve in the fluid connection between the gases flow generator and the first and second naris, the flow control valve controlled by the controller and wherein the controller controls the gas pressure by controlling the flow control valve.

Preferably the flow control valve comprises first and second flow control valves, a first flow control valve in the fluid connection between the gases flow generator and the first naris and the second flow control valve in the fluid connection between the gases flow generator and the second naris, the first and second flow control valves controlled by the controller.

Preferably the controller periodically changes the pressures applied to the first and second naris such that the breathing gas pressure applied to the first naris is lower than the breathing gas pressure applied to the second naris during inhalation such that the breathing gas inflow to the patient is substantially through the second naris and wherein the breathing gas pressure applied to the first naris is higher than the breathing gas pressure applied to the second naris during exhalation such that the gas outflow from the patient is substantially through the second naris.

Preferably the change in the pressures applied to the first and second naris is driven by a predetermined period that is user programmable.

More preferably the predetermined period is 5 minutes to 360 minutes.

Preferably the apparatus is used for treating snoring or obstructive sleep apnoea.

Preferably the apparatus is used for oxygen therapy.

Preferably the gases flow generator comprises at least two gases flow generators and wherein at least two of the at least two gases flow generators are separately controllable.

In a fourth aspect, the invention may broadly be said to consist in an apparatus for the controlled delivery of breathing gases to a patient, comprising:
 a fluid connection between a gases flow generator to each of a first and second naris of the patent; and
 a controller for controlling the pressure of the gases supplied to the first and second naris of the patent, the controller configured to:
 apply breathing gas pressure within the first naris of a patient during inhalation;
 apply breathing gas pressure within the second naris of the patient during inhalation;
 apply breathing gas pressure within the first naris of the patient during exhalation; and
 apply breathing gas pressure within the second naris of the patient during exhalation,
 wherein the breathing gas pressure applied to the first naris is higher than the breathing gas pressure applied to the second naris during inhalation and exhalation such that the breathing gas inflow to the patient is substantially through the first naris and the gas outflow from the patient is substantially through the second naris.

Preferably the controller forces the breathing gases inflow through the first naris and outflow through the second naris.

Preferably the apparatus further comprises a flow control valve in the fluid connection between the gases flow generator and the first and second naris, the flow control valve controlled by the controller and wherein the controller controls the gas pressure by controlling the flow control valve.

Preferably the flow control valve comprises first and second flow control valves, a first flow control valve in the fluid connection between the gases flow generator and the first naris and the second flow control valve in the fluid connection between the gases flow generator and the second naris, the first and second flow control valves controlled by the controller.

Preferably the controller periodically changes the pressures applied to the first and second naris such that the breathing gas pressure applied to the first naris is lower than the breathing gas pressure applied to the second naris during inhalation and exhalation such that the breathing gas inflow to the patient is substantially through the second naris and the gas outflow from the patient is substantially through the first naris.

Preferably the change in the pressures applied to the first and second naris is driven by a predetermined period that is user programmable.

More preferably the predetermined period is 5 minutes to 360 minutes.

Preferably the apparatus is used for treating snoring or obstructive sleep apnoea.

Preferably the apparatus is used for oxygen therapy.

Preferably the gases flow generator comprises at least two gases flow generators and wherein at least two of the at least two gases flow generators are separately controllable.

In a fifth aspect, the invention may broadly be said to consist in a system for the controlled delivery of a breathing gas to a patient wherein the system provides a greater airflow through a forced patent naris and a lesser airflow through a forced congested naris throughout a breath cycle

BRIEF DESCRIPTION OF THE DRAWINGS

Embodiments of the present invention will now be described, by way of example only, with reference to the accompanying drawings, in which.

DETAILED DESCRIPTION

Figure 1:
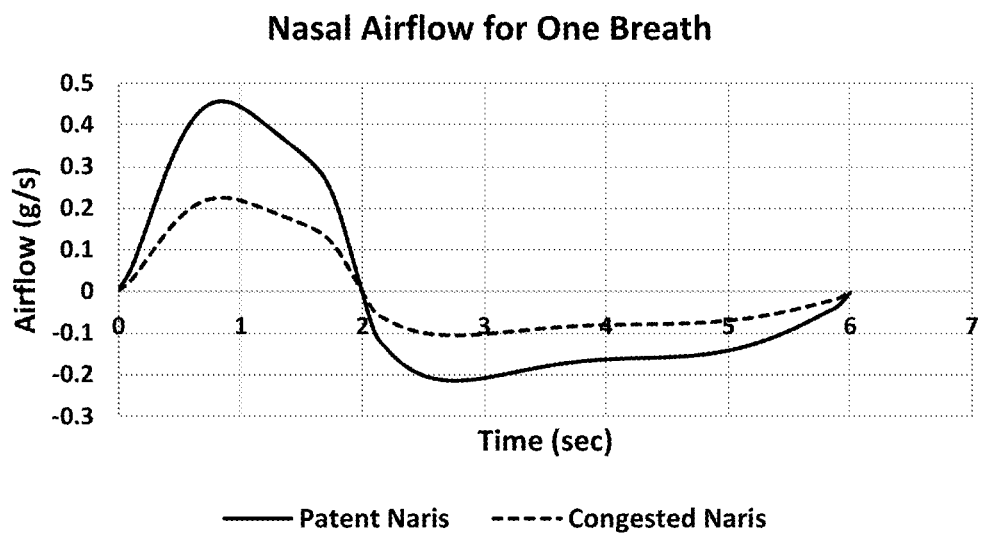
FIG. 1 shows a graph of the normal bias in airflow between patent and congested nasal airways.

Most healthy people experience, but are not aware of, a bias in nasal airflow where one nasal airway, termed 'patent' conducts more airflow than the other which is described as 'congested'. In this example illustrated in FIG. 1, the inhalation phase takes two seconds and exhalation spans a further four seconds.

Figure 2:
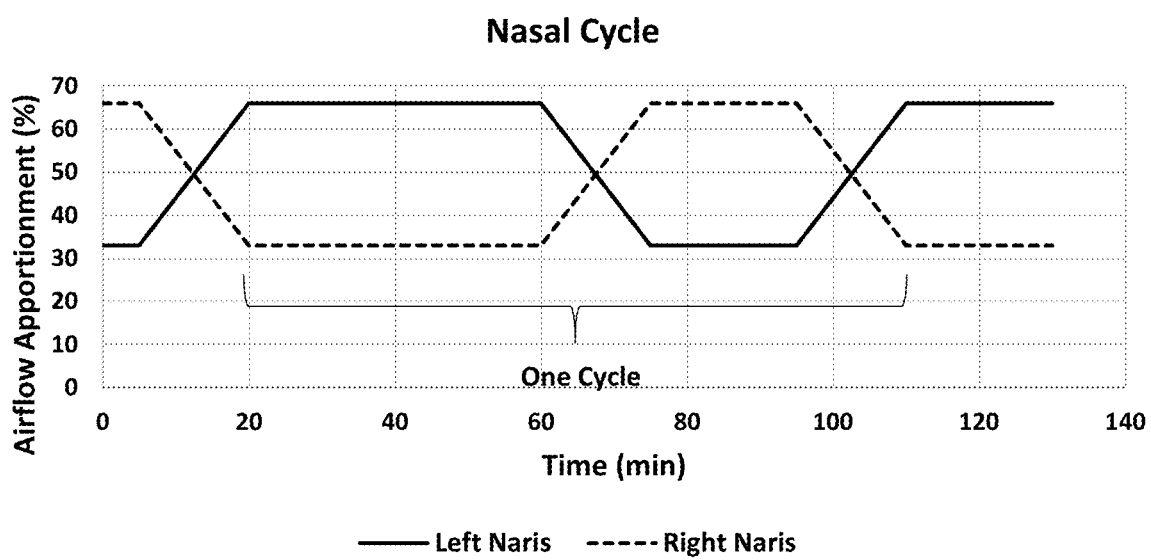
FIG. 2 shows a graph of a nasal cycle spanning a 90 minute period.

This bias in airflow passing through each naris varies in magnitude between individuals but normally the patent airway carries two thirds of the total tidal breath while the congested airway conducts the remaining one third. The status of each airway periodically swaps in what is commonly known as 'the nasal cycle', shown by FIG. 2. Here the previously patent airway becomes congested and vice-versa. This cycle normally has a period of approximately ninety minutes but can vary up to nine hours in duration.

The ratio of tidal breathing air passing through each nasal airway can be manually controlled by either constricting or blocking airflow as it passes through each naris. For example, a finger is commonly used in Yoga techniques to manually restrict or completely occlude airflow through an individual naris. This method is commonly used to manually force change in the status of the nasal cycle.

Figure 3:
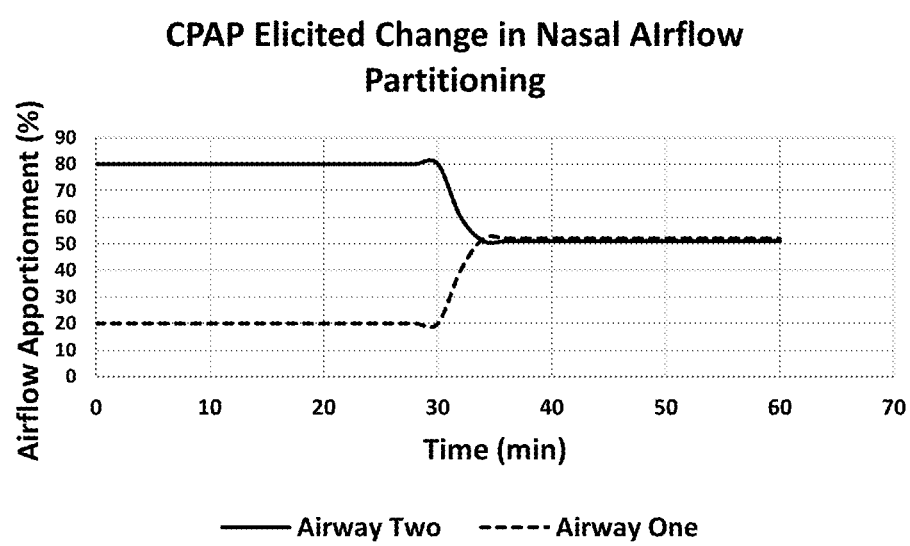
FIG. 3 shows a graph of a change in normal nasal airflow apportionment between the patent and congested airways when pressurised nasal breathing is introduced.

Nasal breathing of pressurised air also abolishes normal airflow partitioning. Here the patent airway experiences a reduction in airflow while the congested airway experiences an opposing response of increase in airflow, shown in FIG. 3.

There are many issues associated with the abolishment of normal nasal airflow partitioning and the nasal cycle. From a functional perspective, the separate roles of air-conditioning and mucociliary clearance carried out by each airway are obliterated which results in both airways experiencing drying and ineffective mucociliary transport of entrapped pathogens. These phenomena are demonstrated by users of nasal applied continuous positive air pressure (n-PAP) therapy who commonly complain of symptoms associated with airway drying, inflammation and congestion.

While supplementary humidification relieves these symptoms and helps to maintain mucociliary clearance in patients receiving n-PAP therapies, the influence nasal breathing of pressurised gases has on other physiological and neurological functions associated with nasal airflow partitioning and the nasal cycle are currently unknown. An indication of this influence can be found in some studies into n-PAP therapy adherence that has found, by choice, around 75% of patients use this therapy for less than 4 hours per night and around 50% discontinue long-term n-PAP use completely. Despite its popularity in relieving negative symptoms associated with airway drying, the ability of supplementary humidification to improve adherence to n-PAP treatment is questionable given no improvement occurs when supplementary humidification is introduced. These findings suggest that patient dissatisfaction with n-PAP therapy might be more complex than simply a case of mucosal drying. For example, abolishment of the nasal cycle might negatively influence sleep staging patterns or other physiological and neurological activity.

The present invention system asserts control of nasal airflow during pressurised nasal breathing by regulating the apportionment of the total breath between each nasal airway during both inhalation and exhalation breathing phases. This control is achieved by varying the air pressure supplied to each naris in response to the continuous measurement of airflow passing to each naris and results in one airway, termed 'forced patent' conducting a greater amount of airflow. The other airway conducts a lesser amount of airflow is termed 'forced congested'.

The pressure is preferably delivered through a substantially sealed mask that forms a seal with each naris or the face. The substantially sealed mask or system will also have a vent or bias flow to allow the exhaled air and CO2 to be flushed out, as used in conventional CPAP therapy systems that seal against the face, but also have a vent or bias flow.

Alternatively the mask may be an open, unsealed, cannula type, similar to those used for oxygen delivery. When the system is set up for unsealed use it may take regular measurements of nasal airway resistance and follow the body's natural nasal cycle, as that is less likely to be abolished, due to the lower pressures being applied. Alternatively the system could cycle form left to right on a regular basis, as driven by the device program or user input. The user input maybe programmed, or may be an interface that the user pushes to change from one naris to the other due to the user experiencing discomfort. As the system delivers air predominantly to one naris at a time, it allows the other to recover, and rehydrate, while the other side is used to pass the air, oxygen, or other medication to the user's airway.

Two generic types of nasal airflow control categories are envisaged along with two combinations:
   i. Forced unilateral breathing, where one airway conducts the majority of airflow during both inhalation and exhalation phases of breathing as demonstrated in the normal nasal cycle.
   ii. Forced bilateral breathing, where air exclusively passes into the nose though one naris during inhalation and then flows out of the nose through the other naris during exhalation.
   iii. Combinations of forced unilateral and bilateral breathing, where switching between these two types of breathing can occur in any order and arrangement.
   iv. Combination of forced unilateral breathing on inhalation and balanced nasal airflow on exhalation, where nasal airflow is partitioned during inhalation but forced to become equal during exhalation.

When set to forced unilateral breathing mode, the present invention control system ensures that the forced patent airway receives a higher pressure than the forced congested airway during the inhalation phase of breathing. Conversely, during the exhalation phase, the patent airway receives a lower pressure than the forced congested airway. The present invention system also allows for the pre-setting of both the nasal cycle time duration and airflow partitioning between each naris. The delivery of maximal pressure also varies from when the system is first switched on to achieve measurement of natural nasal cycle status before entering into a pressure ramp phase that allows the user to acclimatise to breathing at augmented pressures.

The present invention continuously regulates airflow through each naris so that the instantaneous amount of tidal breathing air passing through each naris achieves the desired percentage apportionment of the total airflow. As mentioned earlier, for a healthy awake person the airflow apportionment ratio for the patent airway is around two thirds of the total flow while the congested airway passes around one third, shown earlier in FIG. 1. This airflow apportionment ratio may vary from being near equal in both airways to exclusively passing through the patent airway.

Artificially reinstating the natural nasal airway flow partitioning while on CPAP allows the nasal airway passages to function as they would do if the user was not on CPAP. For example it allows one side to humidify the air and the other to recover and conduct the mucociliary transport function. After a period of time the forced patent airway will change, as is normally does while not on CPAP. It may be possible to not use a water humidifier with the present invention CPAP system, as normal airway function can be resorted. Alternatively it may also be beneficial to include a water humidifier.

Figure 4:
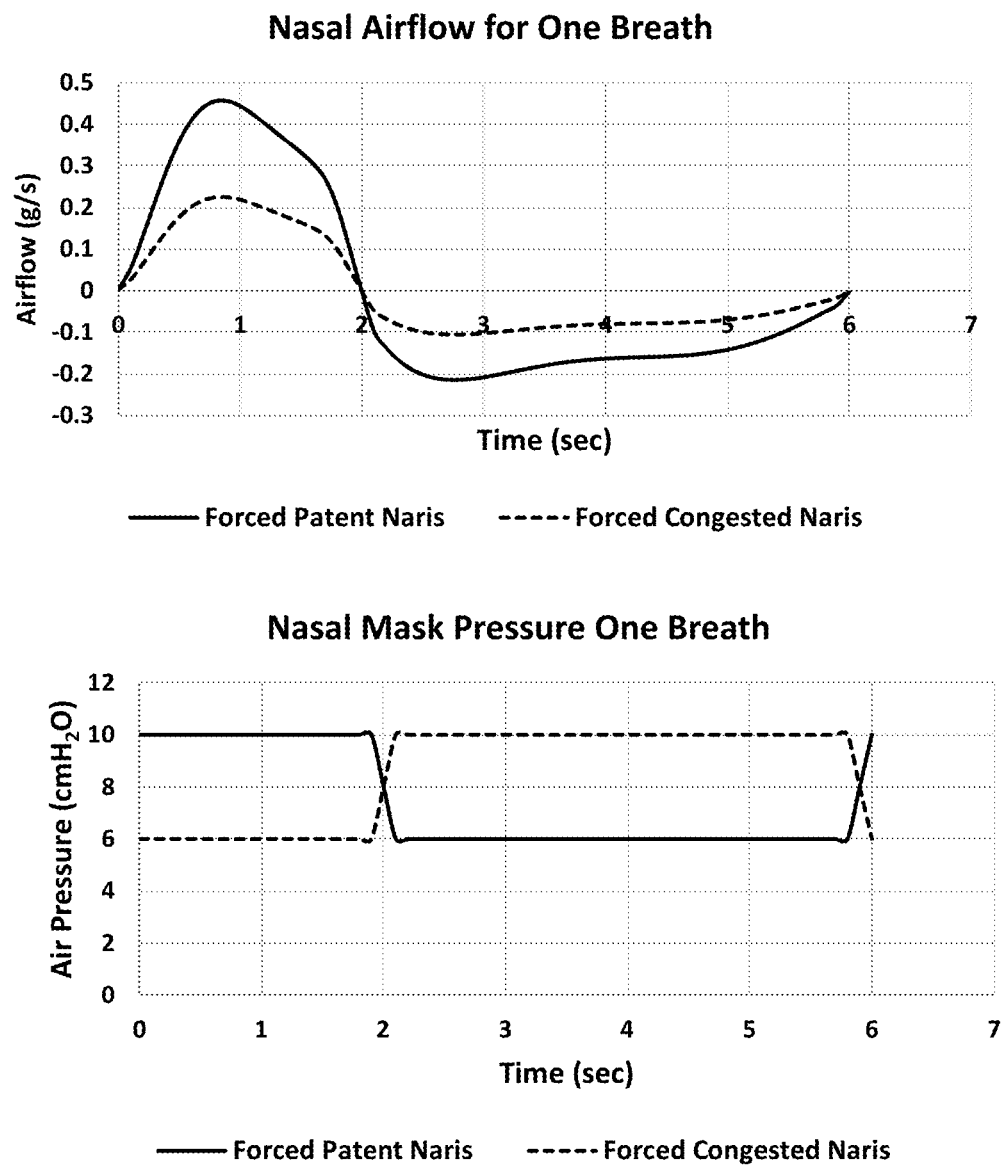
FIG. 4 shows a graph of the variation of air pressure and resultant airflow passing through each naris during forced unilateral breathing of the present invention.

Regardless of the airflow apportionment between the forced patent and forced congested airways, airflow bias in favour of the forced patent airway during pressurised nasal breathing is achieved by the present invention system providing different air pressures to each naris over the total breath cycle. During the inhalation phase of breathing the present invention system provides a higher pressure to the forced patent airway and a lower pressure to the forced congested airway. During the exhalation phase the forced congested airway receives a higher pressure than the forced patent airway. This relationship between individual naris airflow and air pressure supplied to each naris for one complete breath cycle is shown in FIG. 4.

Change in the air pressure delivered to each naris can be progressive rather than a sudden switch, with change in pressure occurring in proportional to the amount of airflow occurring through each airway.

While the therapy has many potential applications, the treatment method for obstructive sleep apnoea (OSA) is described below.

Figure 5:
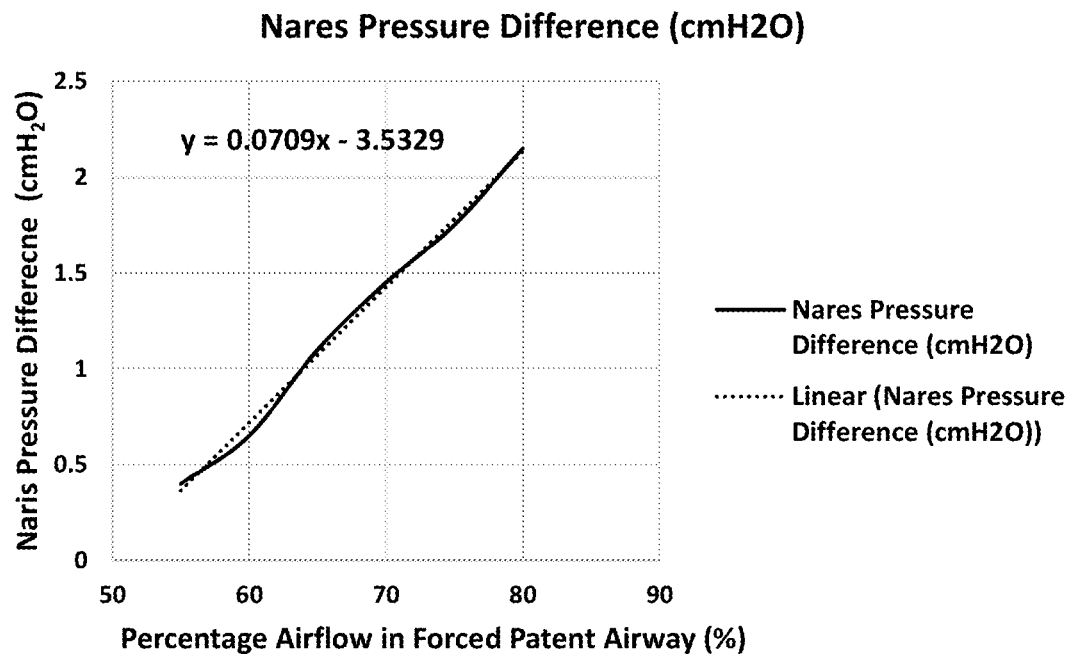
FIG. 5 shows a graph of peak variation of inhalation air pressure differential between forced patent and forced congested airways measured at machine during forced unilateral breathing of the present invention.

While the different pressures delivered to each naris differ as a result of the individual's nasal airway response to pressure augmentation, the difference between these pressures also increases with increasing bias in airflow in favour of the forced patent airway. By way of an example, as shown by FIG. 5, during inhalation, the pressure difference between the patent and congested airways is around 0.4 cm H2O for the patent airway to conducts 55% of the total tidal airflow. The exhalation pressure trend may be different from that shown. This pressure difference needs to increase up to 2.1 cm H2O if the forced patent airway is to conduct 80% of the total tidal airflow. This data is for an individual at set pressure of 10 cm. The pressure differences at the machine become greater as the set, or titration pressure increases. It also decreases as the set pressure is reduced, for the same target ratio. These differences also vary from one individual to another, as they depend on nasal airway resistance.

Figure 6:
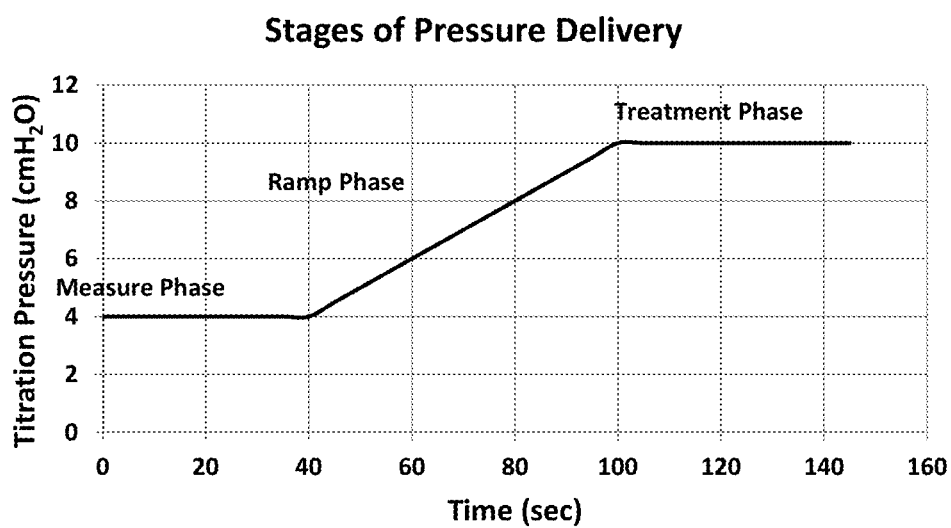
FIG. 6 shows a graph of the progression of titration pressure change from the commencement of operation.

The maximal air pressure delivered to either naris varies from the time the system is first started is defined as 'treatment or titration pressure'. There are three discrete pressure control stages over which the gas pressure being delivered is controlled:

i. Measurement Phase. Here the system determines the current status of the patient's nasal cycle prior to treatment. This is done by initially applying an air pressure to both nares that supports normal breathing that could vary in pressure from very low (say 4 cm H2O) to titration pressure. During this time the individual naris airflow is simultaneously measured by the system over a set number of breaths (say 10). The phasing of the naturally occurring patent and congested nasal airways are then identified to either the left and right nares.

ii. Ramp Phase. Immediately upon completion of the measurement phase the system responds in two ways. Firstly, the maximal pressure delivered to either naris ramps up over a pre-set ramp time (can vary from 0 to 60 minutes) until titration pressure is achieved. Secondly, the air is independently delivered to each naris over each phase of the breath cycle. During inhalation this airflow bias provides the patent airway with ramp pressure and the congested naris with a lower air pressure. Conversely during exhalation, the congested airway receives ramp pressure while the patent airway receives a lower pressure. During this phase of operation it may be desirable to switch the left airway to being forced patent if is not already in this status. It is also possible to gradually increase the ratio during the ramp phase, starting at 50:50 and going up to the desired ratio, or the ratio may be introduced at the end of the pressure ramp phase or both pressure and ratio ramp maybe independently controlled.

iii. Treatment Phase. Once the ramp pressure equals the designated titration pressure the maximal pressure supplied to either naris over the full breath cycle is limited to the titration pressure. Here, both airways continue to be independently supplied differing air pressures in order to achieve the desired airflow partitioning ratio over each phase of the breath cycle as previously described in the ramp phase. Throughout the duration of the treatment phase there is also the ability to switch the status of each airway from being forced-patent to forced-congested. The relationship between each of these pressure phases is shown in FIG. 6.

During the sleep period the designated titration pressure may vary. During the REM sleep phase the body loses muscle control while during n-REM sleep the brain regulates muscle action. Because of this, upper airway obstruction is most likely to occur during REM periods of muscle relaxation and less likely when muscle control is present.

The next section describes the relationship between sleep stage and lateralisation of nasal breathing. Titration pressure may also vary depending on the nature of control algorithm implemented. This could vary from a steady value, as found in continuous positive air pressure (CPAP) applications, a reduction in titration pressure during exhalation as found in bi-level continuous positive air pressure (Bi-PAP) devices, through to adaptive pressure control based on detection algorithms as used in auto-setting continuous positive air pressure (A-PAP) therapy devices. Machine airflow measurements may be taken from one or both airflow streams leading to each naris and A-PAP detection may be based upon flattening of the waveform of measured airflow. A pressure relief function, where both airways experience a reduction in pressure but sustain a difference between each airway may also be included to reduce the exhalation effort. Phases i and ii previously described are optional and forced air flow partitioning may be implemented later in the treatment phase.

Figure 7:
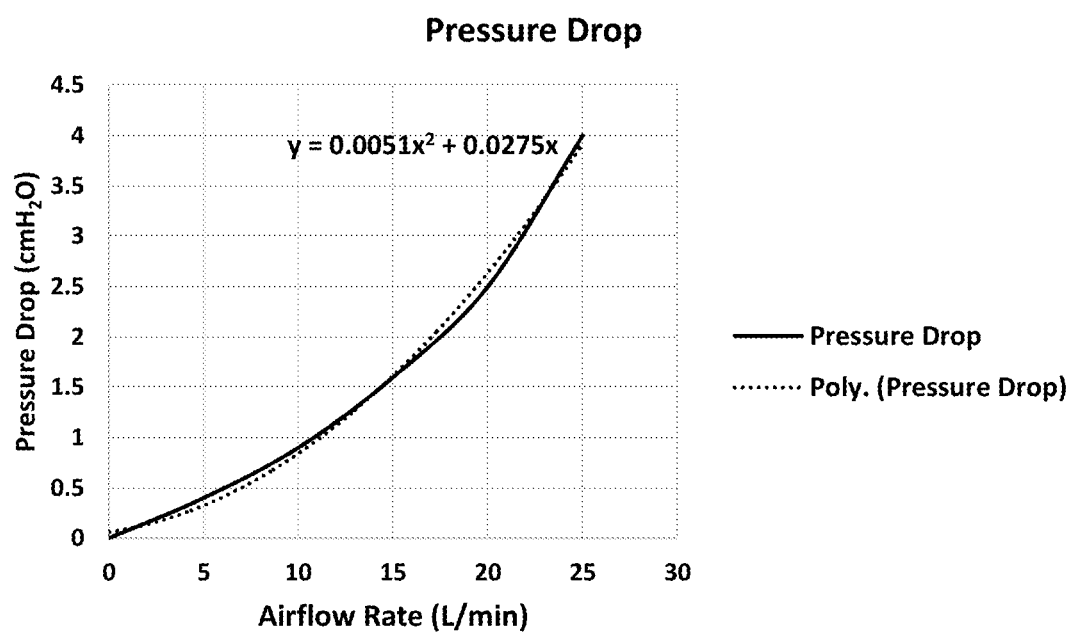
FIG. 7 shows a graph of the typical change in nasal resistance as a function of airflow rate.

The amount of air flowing through each nasal passageway is one factor in determining the individual airway resistance. Here, higher airflow rates cause an increased resistance while decreased flow leads to a reduction in resistance, as shown in FIG. 7. Because of this, the pressure difference delivered between the forced patent and forced congested airways can vary as the rate of air flowing through each naris varies.

During periods of low airflow or where pauses in breathing occur the airflow resistance within each airway becomes extremely small. Under these conditions it becomes possible for air to be forced up one naris while air simultaneously exits out the other. This back-flow effect is driven by the difference in air pressure delivered to each naris. Because of this it is highly desirable during periods of low flow rates, or if complete pausing in breathing occurs, that there be no pressure differential delivered across both nares. The pressure change can be delivered in proportion to the measured airflow rate or by other means such as:

Calculating the total inhaled air volume and using this measurement as a basis for determining when exhalation has completed and where airflow rates are low or have completely ceased.

At a high level we will deliver the same pressure to each side whenever the patent flow (excluding the bias or vent flow) is below a threshold. For example when net flow in or out is less than 10 l/min for example.

This threshold may vary and be a function of the pressure difference, and as the pressure difference is a function of the desired ratio, the threshold may vary as a function of the ratio.

The pressure difference may step down to zero after reaching a threshold, or the pressure difference may be reduced gradually to zero.

Another way to deal with this issue is to only introduce the pressure difference after a certain amount of time and after each inhalation has started, for example 0.3 seconds after the start of inhalation and only for a set amount of time, for example 1.0 seconds. This start will be determined by monitoring the flow signal. Or it could be maintained until the system estimates that the patients inhalation will end within a set amount of time, based on the flow signal (rate of change) and/or past breath cycles, for example within 0.3 sec of the end of the exhalation phase. The same could be repeated for the exhalation phase.

Another variation may measure the rate of change of airflow rate near the end of the inhalation or exhalation breath phases.

Another variation (that may apply to other embodiments in the application) is that only the inhalation flow ratio may be controlled and the exhalation phase may be conducted with the same pressure (or ratio) for left and right nares. This may allow for improved recovery of exhaled moisture while still only drying one side on inhalation.

Still another variation is conducting the inhalation at the same pressure (or ratio) and controlling the exhalation phase to have different ratios.

Any combination of these variations may be implemented. There are many instances where an individual may pause their breathing. This situation may occur during both awake and sleeping states and a breath cycle containing pauses is shown in FIG. 8.

Figure 8:
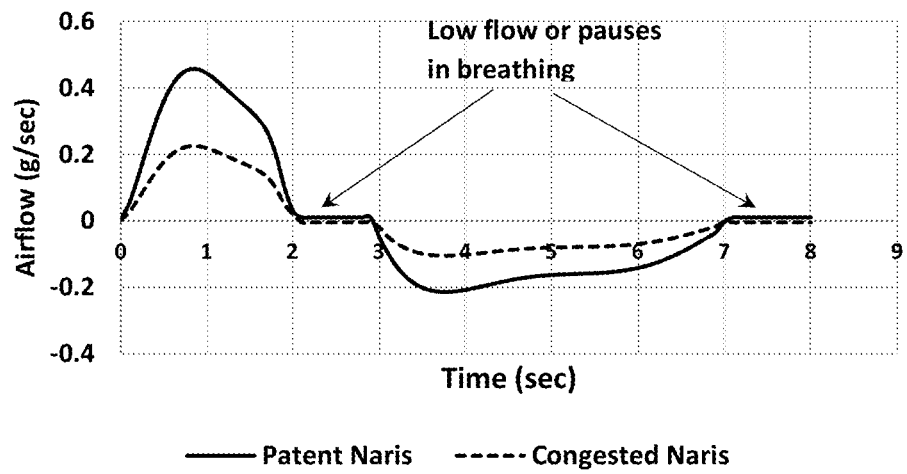
FIG. 8 shows a graph of the variation of air pressure delivered and resultant airflow passing through each naris during forced unilateral breathing of the present invention when pauses in breathing occur.
Figure 8:
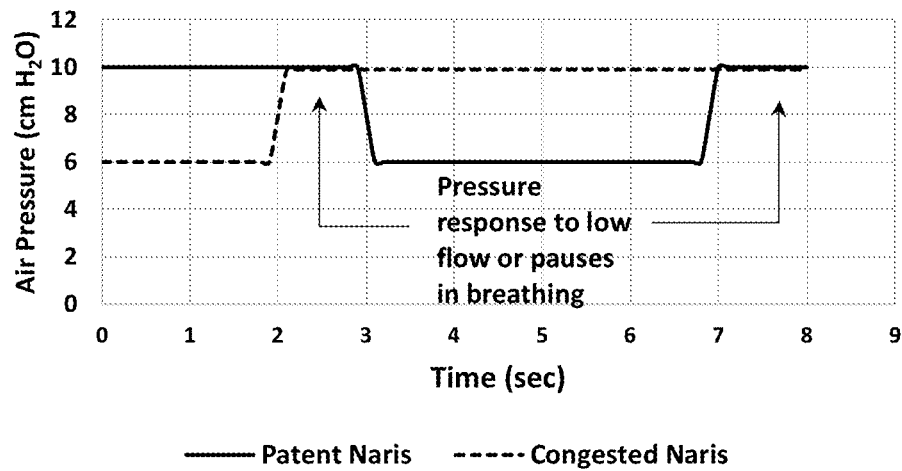

During periods where the user's breathing airflow is either very low or completely paused, as shown in FIG. 8, the system responds by delivering the higher level ('titration') air pressure to both airways, thus preventing the potential for airflow to be driven through the airway receiving the higher pressure and out the airway receiving the lower pressure. If it were permitted to occur, this back-flow between airways would be very detrimental in maintaining airway hydration so it is essential that the system detects and reacts by delivering 'titration pressure' to both airways during periods of low rates of breathing or during complete pauses in breathing.

In all examples of ratio that are given, ratio could mean either an instantaneous flow ratio, or could be a ratio of tidal volume. For example flow rates may be measured instantaneously to control pressure instantaneously, or the area under the flow rate graph illustrated in FIG. 4 may be used to calculate the tidal volume for inhalation and exhalation (separately). This tidal volume from left to right could be compared to a target tidal volume ratio and pressure adjustments could be made to the next breath to reach the desired tidal volume ratio. Data from several breaths could also be used to control future tidal volumes, flow rates or pressures.

Figure 9:
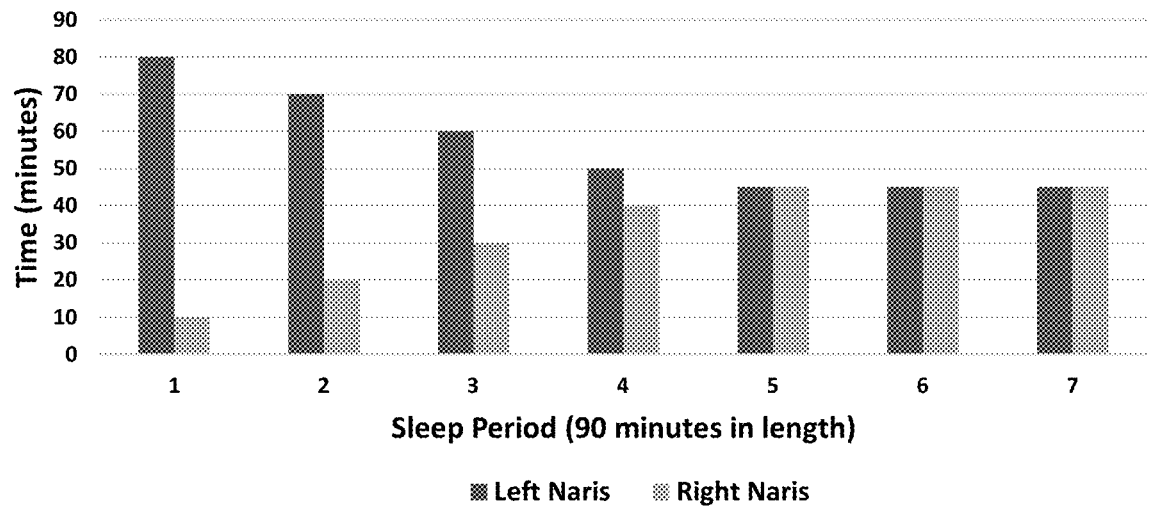
FIG. 9 shows a graph of the change in nasal airflow apportionment ratio over each sleep stage.
Figure 10:
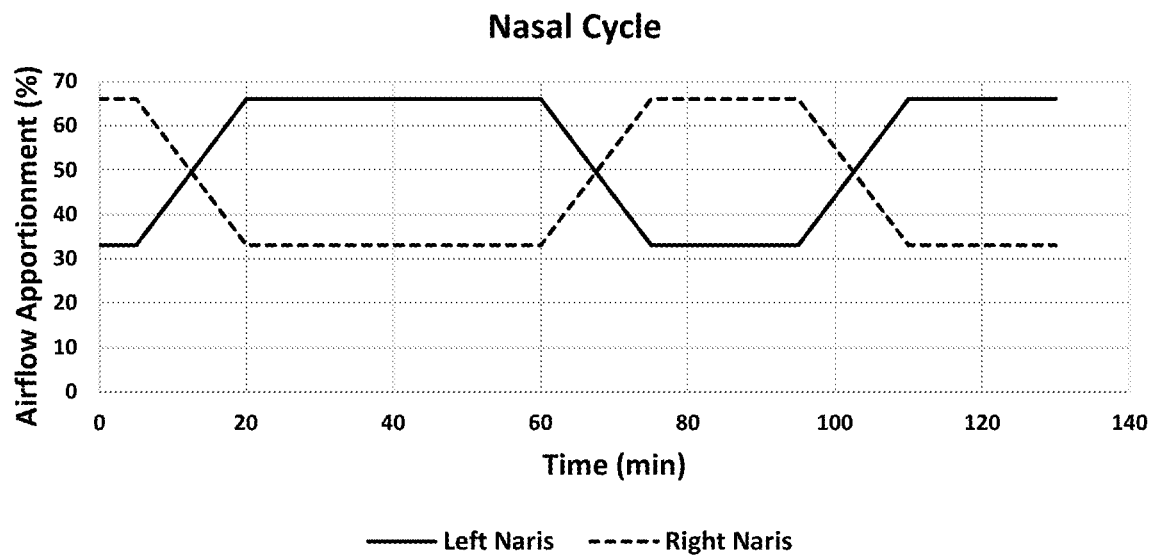
FIG. 10 shows a graph illustrating an example of differing time periods given to each phase of the nasal cycle.

The nasal cycle is set to discreet time periods (initially of 90 minutes duration but clinical studies may give rise to change) that align with the healthy pattern of neurological sleep stages given the correlation between the nasal cycle, cerebral dominance and sleep stage. The duration of time allocated to left and right nostril breathing dominance varies within each of these time periods as previously shown in FIG. 2. During entry into sleep the left naris airflow dominates and the shift to the left airway becoming patent during the initial treatment phase has been described earlier in the titration pressure ramp phase. Initially the amount of time allocated to each airway for each nasal cycle may vary over the sleep night. It seems that the amount of time for right naris dominant breathing increments over each progressive sleep period until there is an equal time allocated to left and right breathing. This initial best-guess setting is represented in FIG. 9.

It is also envisaged that different cycle frequencies and durations could also be utilised during system start-up or to enable recovery from mouth leak or any other situation where the airways have suffered abnormal drying. It may be beneficial for rehydration to have a reduced period of nasal cycle, during periods of ramp or recovery from periods of mouth leak. For example the nasal cycle could be as short as one breath cycle 6 seconds or range up to more than 360 minutes The nasal cycle during ramp or any other phase may be user programmable, so the patient or clinician can select or pre-program the device, or preprogramed options may be selected based on the clinical or user need. Preferably the programmed nasal cycle is between 5 minutes and 360 minutes, even more preferably the programmed nasal cycle is between one and two natural nasal cycles. A natural nasal cycle typically being 90 minute, such that the programmed nasal cycle is between 90 minutes and 180 minutes. The cycle may vary during different phases, such as ramp or while at titration pressure. The total expected sleep time may be input, learnt from past nights data or based on an expected or set time of awakening in the morning, to compress or extend the ideal sleep staging in FIG. 9. The nasal cycle programing can be input to help achieve the desired physiological and neurological outcomes, such as sleep staging, or other body function that can be controlled or is linked to nasal airflow or nasal pressure variations. This may be useful in the treatment of the conditions listed below.

It may also be beneficial to have periods where the ratio is controlled, to force airflow partitioning, and other periods were there is no partitioning. For example the device may use the airflow to sense if the patient is awake, as used in the Fisher & Paykel Healthcare Sense Awake technology, and deliver flow that is not partitioned while the patient is awake. Once the patient is asleep the airflow partitioning could be introduced. It may be that during periods of higher than expected flow, such as mouth leak or mask leak that the partitioning is turned off, until normal flow levels resume. Or it may be that air flow partitioning is introduced for periods to allow the nasal passages to recover before switching back to a non-partitioned state.

As previously described, forced bilateral breathing is where air exclusively passes into the nose though one naris during inhalation and then flows out of the nose through the other naris during exhalation. In this case the nasal cycle has no relevance given each naris takes turns in passing the full tidal volume during the different breathing phases of inhalation and exhalation.

Figure 11:
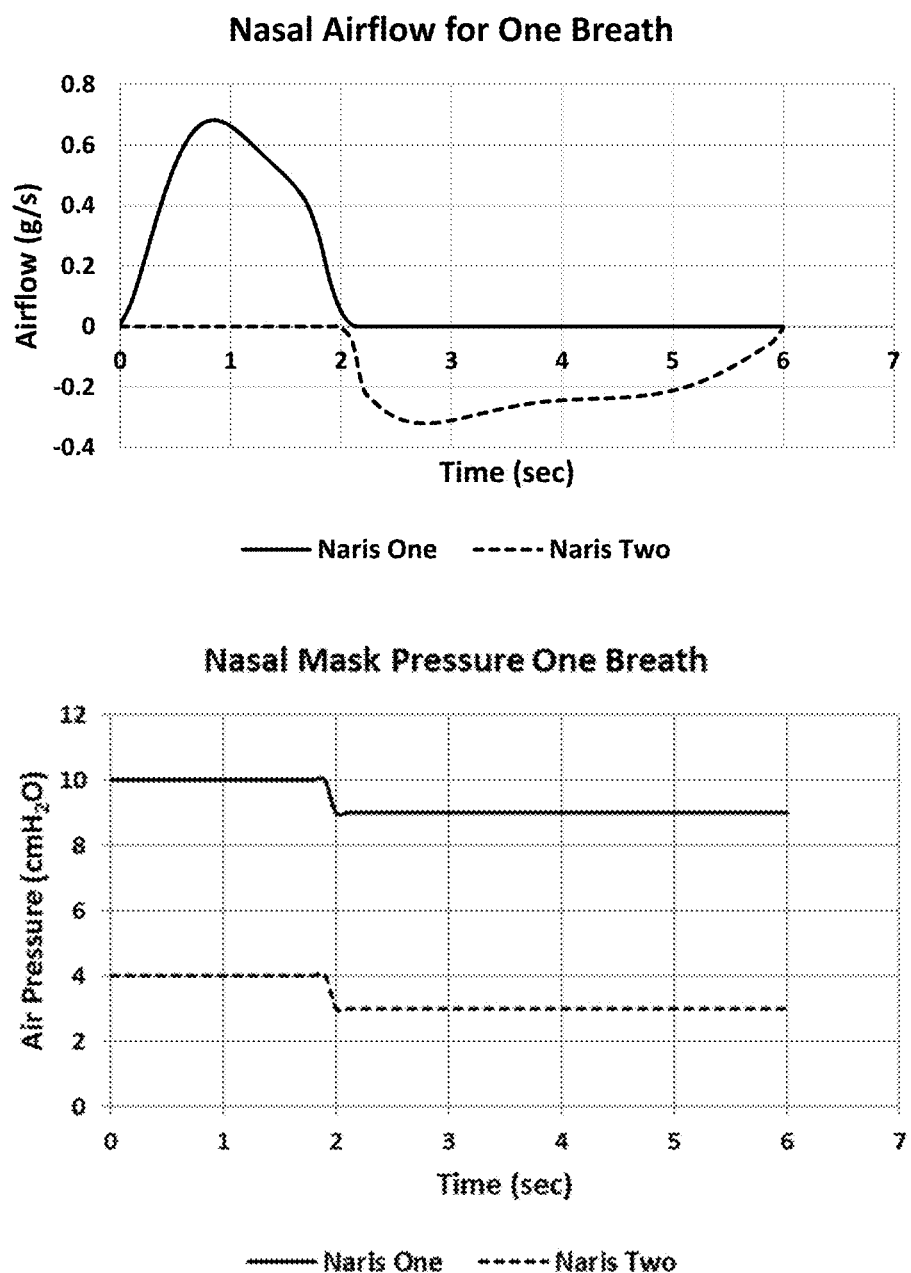
FIG. 11 shows a graph of variation of air pressure and resultant airflow passing through each naris during forced bilateral breathing in an embodiment of the present invention.

When set to forced bilateral breathing mode the control system ensures that the airflow exclusively passes through one naris which is termed 'forced inhalation dominant'. This is achieved by this airway receiving a higher pressure than the other during the inhalation phase of breathing. While actual pressures may vary, this same pressure relationship is maintained during the exhalation phase of breathing where the other naris that previously passed no air now exclusively passes the full amount of exhaled air. The nasal airflows and air pressures corresponding to this type of breathing is shown in FIG. 11.

Figure 12:
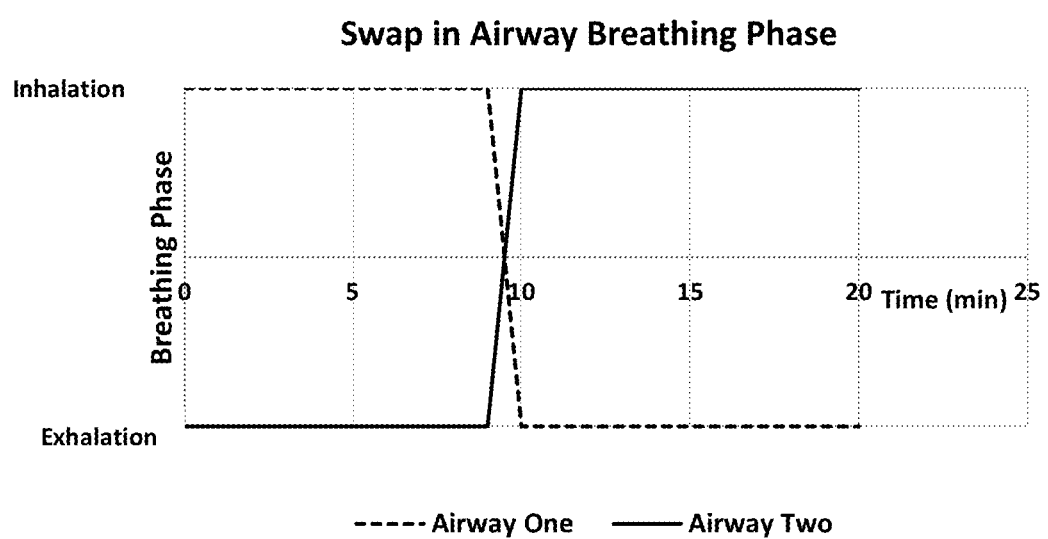
FIG. 12 shows a graph the switch in airways carrying inhalation & exhalation phases of breath through each naris during forced bilateral breathing of the present invention.

Just like the nasal cycle during forced unilateral breathing, the bilateral airflow designation for each naris for inhalation and exhalation phases of the breathing cycle may switch over a specified time period. This switch is shown in FIG. 12.

There are many neurological and physiological pathological conditions where breathing therapy supplied using the present invention could provide a non-pharmaceutical alternative to current treatments or a new treatment option for previously untreatable ailments.

While not limited to this list, a few of these conditions are listed below:
  i. Obstructive sleep apnoea.
  ii. Obesity.
  iii. Type 2 diabetes.
  iv. Stress/anxiety.
  v. Fatigue.
  vi. Sleep quality.
  vii. Cot death.
  viii. Maximising cognitive performance.
  ix. Infant and early childhood autism.
  x. Schizophrenia.
  xi. Stroke recovery.
  xii. Hypertension.
  xiii. Post-surgery recovery.
  xiv. Improved sport physical performance.
  xv. Improved long-distance travel recovery.
  xvi. Fibromyalgia.
  xvii. Alzheimer's disease.
  xviii. Migraine/tension headache.

The system in the preferred embodiment would have a number of pre-programmable parameters, including the parameters listed below.
1. Measure Phase
  a. Measurement pressure.
  b. Measurement time.
  c. Swap to left airway time.
2. Pressure Ramp
  a. Left airway ramp time.
  b. Total ramp time.
  c. Titration pressure.
3. Treatment phase 1
  a. Titration Pressure.
  b. Steady time.
  c. Swap time.
4. Treatment phase 2
  a. Titration Pressure.
  b. Steady time.
  c. Swap time.
5. Treatment phase 3 (up to eight treatment phases)

To enable a user or a physician to obtain information on the patient it is envisaged the system would have a number of readable parameters including:
1. Total and individual nasal airflow.
2. Time of use.
3. Individual pressures.
4. Airflow partitioning ratio.

Figure 13:
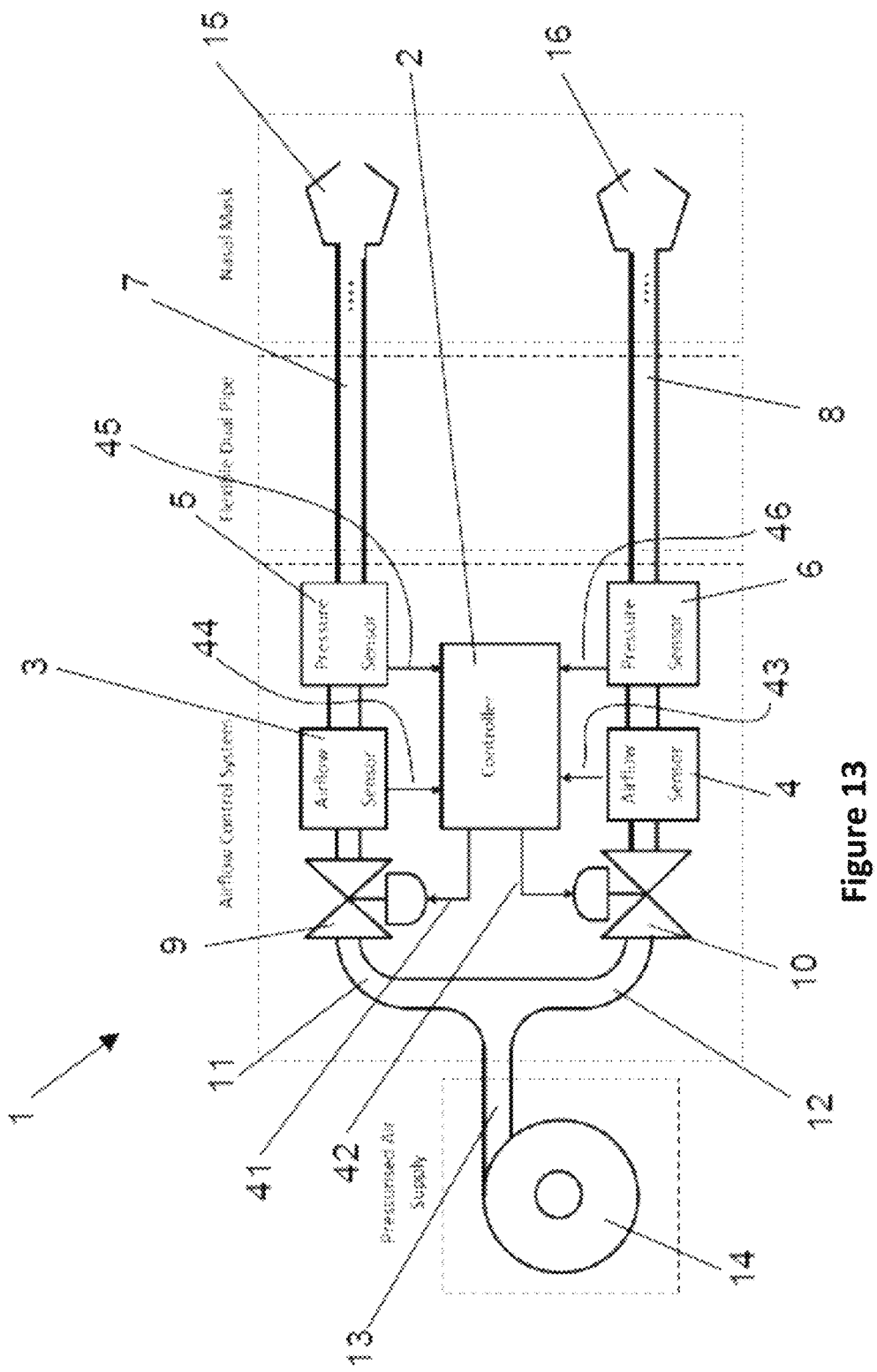
FIG. 13 shows a block schematic of one embodiment of the present invention.

An embodiment of the invention will now be described with reference to FIG. 13. The device of the present invention 1 consists in a controller 2 having a processor, memory for storage including storing a control program and communication system for communicating with the connected sensors and other devices.

The device 1 further has a gases flow generator 13 connected via pipe 13 and the air flow is split into pipe 12, 13 to a plurality of valves 9, 10. The valves 9, 10 are connected to the controller via communication lines 41, 42. Through each of the split pipes 11, 12 the gases eventually flow to a nasal mask having a connection 15, 16 to a naris. The gases flow to each naris of a user is separately controlled via the valve 9, 10 in the pipes which are fluidly connected to each naris. Additionally in the fluid connection to each naris there are airflow sensors 3, 4 and pressure sensor 5. The airflow sensors 3, 5 sense the airflow and communicate the airflow information to the controller via communication channels 43, 44. The pressure sensors 5, 6 sense the pressure and communicate the pressure the controller via communication channels 45, 46.

Figure 14:
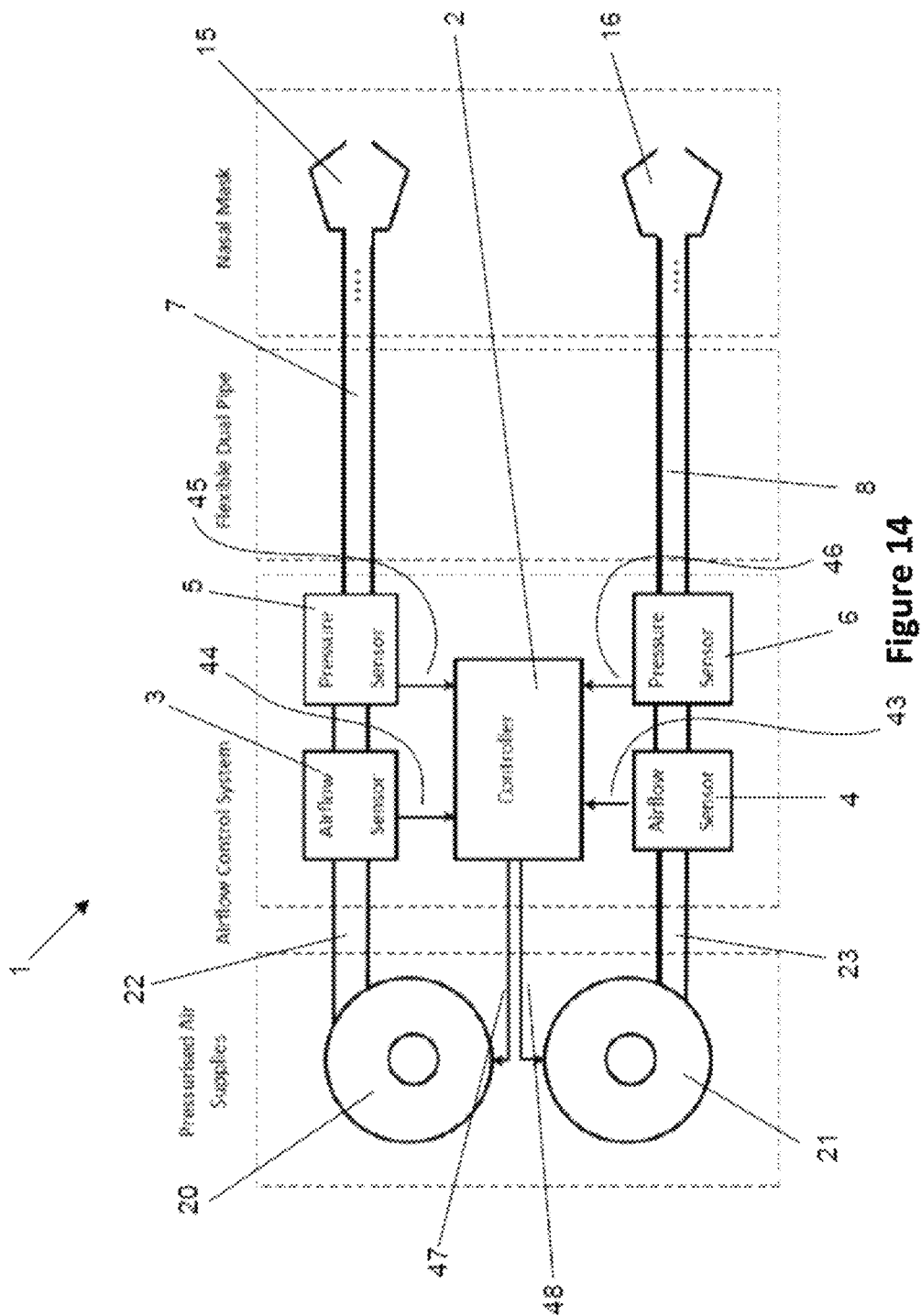
FIG. 14 shows a block schematic of a further embodiment of the present invention.
Figure 15:
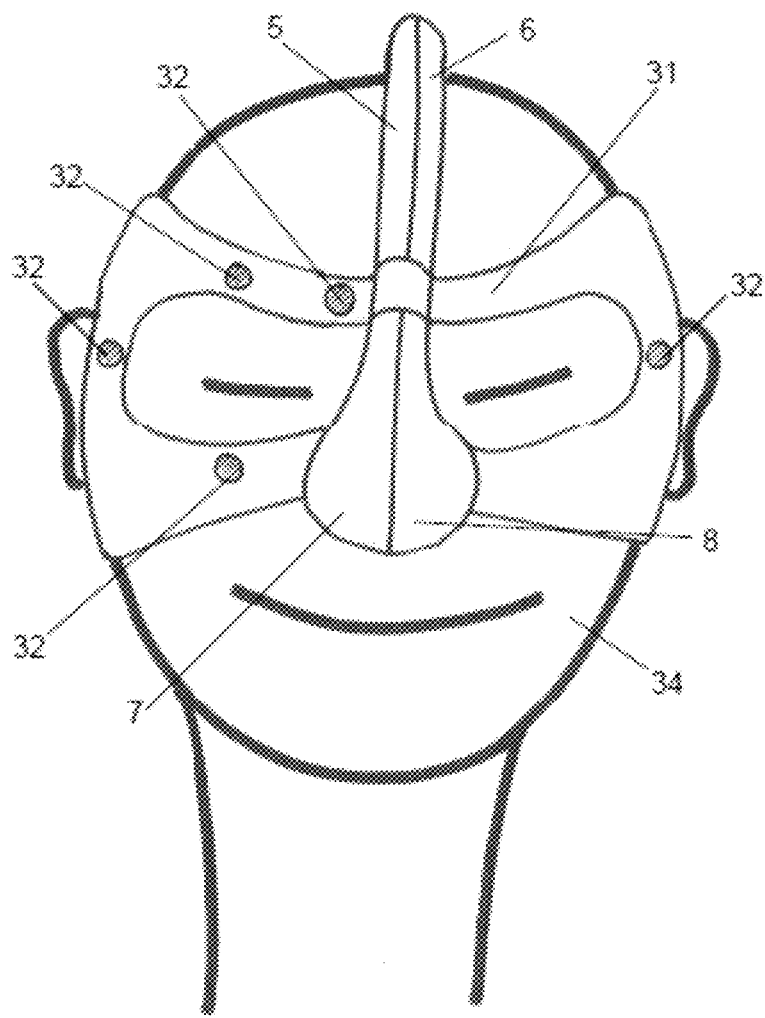
FIG. 15 shows a diagram of a front view of a user wearing a mask with sensors on the mask strap.
Figure 16:
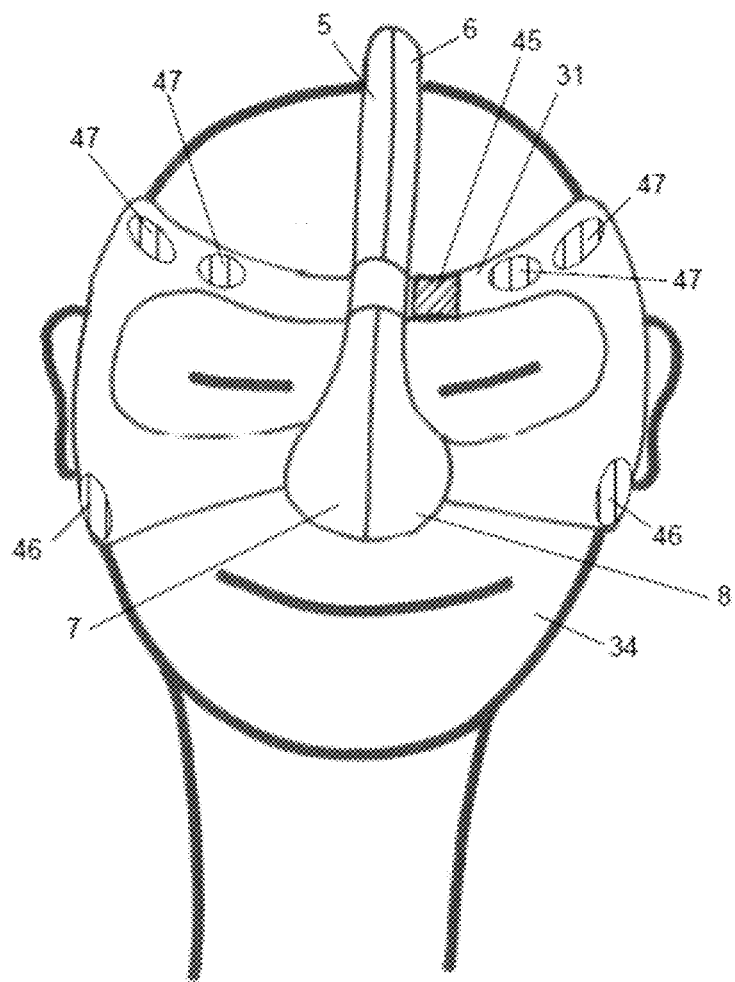
FIG. 16 shows a diagram of a front view of a user wearing a mask with alternative sensors on the mask strap.
Figure 17:
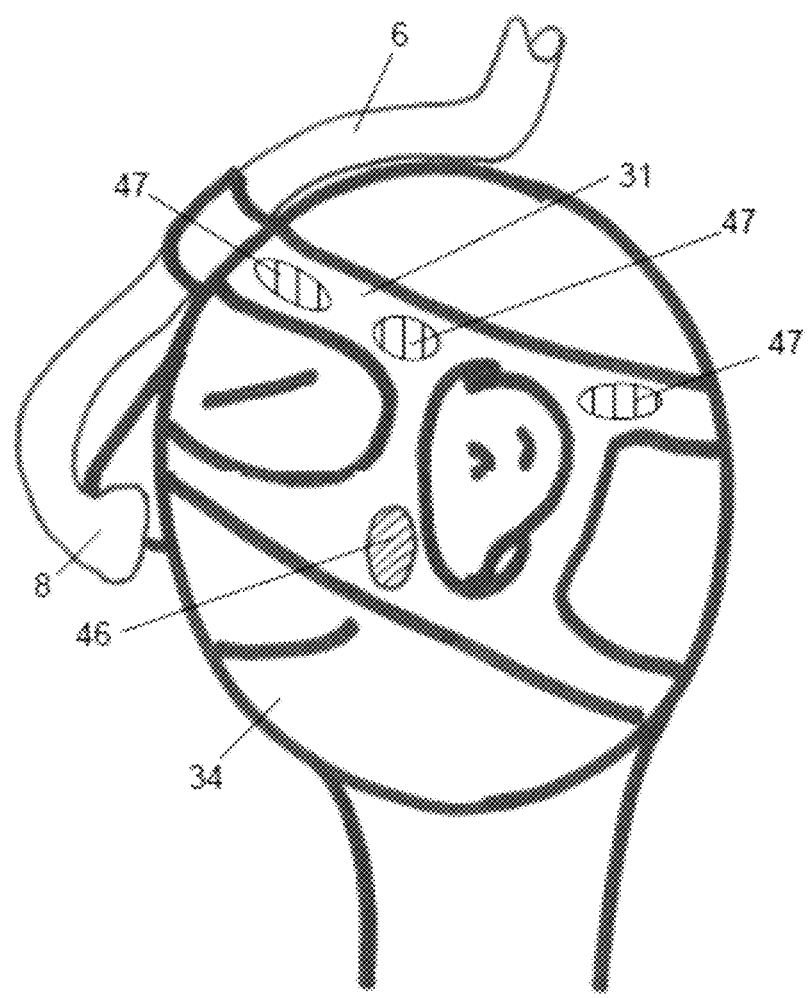
FIG. 17 shows a diagram of a side view of a user wearing a mask with sensors on the mask strap.

Referring to FIG. 14 an alternative embodiment of the present invention will be described.

The device 1 of the present invention in an alternative embodiment consists in a controller 2 having a processor, memory for storage including storing a control program and communication system for communicating with the connected sensors and other devices.

The device 1 further has two gases flow generators 20, 21, each generator is in fluid communication with a single naris. The generators are also in communication with the controller via communication channels 47, 48. The channels allow the controller to both receive information from the gases flow generators 20, 21 and to control the gases flow generators 20, 21.

The gases flow generators 20, 21 are connected via pipes 22, 7 and 23, 8 in fluid connection respectively to a single naris of a user. The gases flow to each naris of a user is separately controlled by the controller by the controller 2 controlling the gases flow generators 20, 21.

Additionally in the fluid connection to each naris there are airflow sensors 3, 4 and pressure sensor 5. The airflow sensors 3, 5 sense the airflow and communicate the airflow information to the controller via communication channels 43, 44. The pressure sensors 5, 6 sense the pressure and communicate the pressure the controller via communication channels 45, 46.

Figure 18:
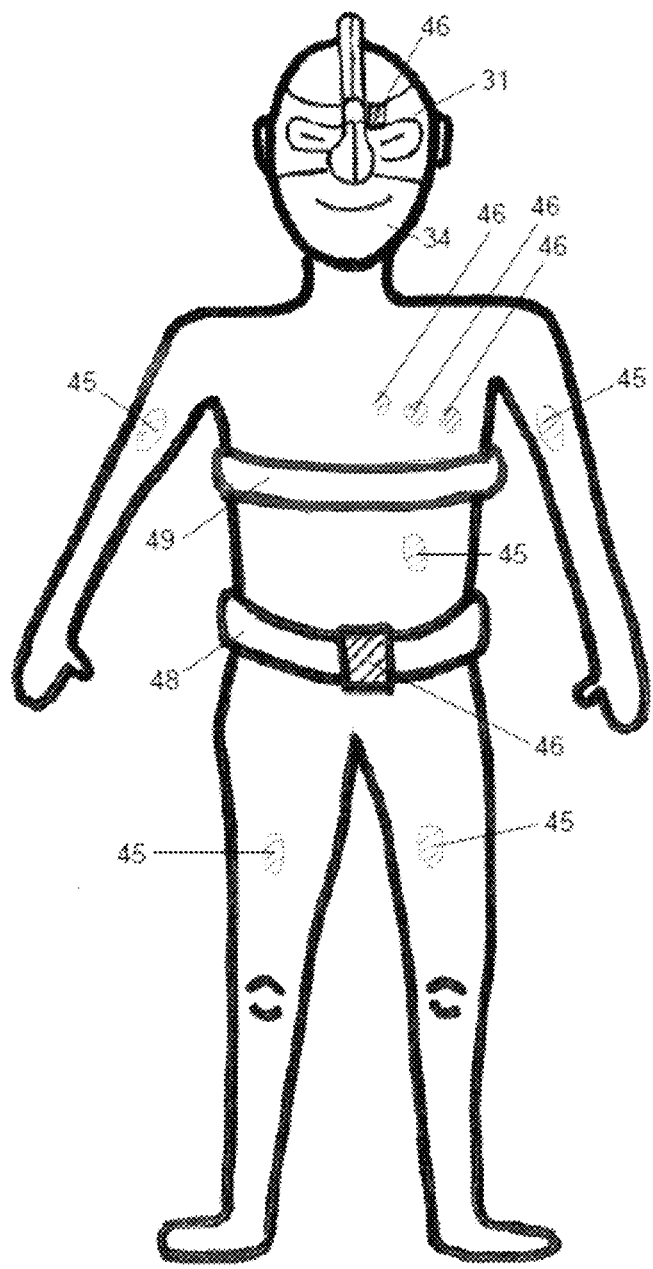
FIG. 18 shows a full body diagram of a user showing the sensors of the present invention as they might be positioned on a user's body.

Also in communication with the controller 1 are various sensors. Referring to FIGS. 3 to 6 the system of the present invention optionally includes on the mask 31 that a user 34 wears EOG sensors 32, EEG sensors 47, ultrasound sensors 46 and an accelerometer 46. Referring to FIG. 18 body mounted sensors may optionally comprise ECG/EKG sensors 46, EMG sensors 45, respiratory effort bands 48, 49, EMG sensors 45 and a body mounted accelerometer 46.

The various sensors described above are in communication with the controller 1 and allow the controller to make various assessments of the user using the system 1 of the present invention. The controller is able to detect nasal airway resistance measurement by for example setting the pressure for each flow generator 20, 21 shown in FIG. 14 to the same pressure, and measuring the flow in each side of the system, using airflow sensors 3, 4. Alternatively the pressure sensors 5, 6 and the airflow sensors 3, 4 could be used. As this measurement needs to interrupt the therapy for a period of time it may only be taken periodically for example every 1-10 minutes, and the test could last from 1 breath cycle to as long as 10 breathes cycles, or 6 second to 60 seconds. The relative resistance of each naris could be calculated by comparing the flow rates in each naris.

Further the controller could measure nasal airway flow using the above described apparatus.

Body position could be detected using the accelerometers 46 communicating with the controller 1 attached to the body and head of the user.

Other physiological measurement could be taken such as Electroencephalography (EEG), Electrocardiography (ECG or EKG), electromyogram (EMG), respiratory effort bands, EOG, or any combination of these sensors.

In one embodiment the present invention could be optimised to target maximize sleep efficiency. Sleep efficiency would be calculated by the controller using many of the previously described physiological measurements, with the controller 1 maximizing sleep efficiency by controlling the flow to each naris based on the measured data. In an alternative embodiment an individual patient's ideal nasal cycle frequency could be determined in and programed into the controller.

In another embodiment the present invention could be optimised to target a reduction in apnoea events. The controller 1 could monitor gases flow signal(s) to detect flow limitations or stops (apnoea event) in then adjust the gases flow and gases pressure via the valves 9, 10 or by controlling the gases flow generators 20,21. In another embodiment the controller could be programmed to switch the primary naris to reduce the rate of apnoea)

In a further embodiment it may be predetermined that user has an ideal frequency of their individual nasal cycle, or that all people may benefit from the same nasal cycling, at a certain frequency, or that forced cycling is better than CPAP. This may allow each naris to "rest and recover" for a set period of time. This would allow the device to have a user, clinician or manufacturer programed cycle. A nasal cycle shall be understood to mean the time taken for the primary naris to be patent and then congested, and back to be patented.

The controller 1 of the present invention is programmed to over each breath cycle, regulate the inter-nasal airflow partitioning between each naris airway. In order to achieve this the controller 1 independently varies the air pressure experienced at each naris. Variation in this pressure is achieved through actuation of the two airflow regulation valves 9, 10 or controlling the gases flow generators 20, 21. The controller thus adjusts the amount of gases flowing through the air channels supplying each naris. Each airflow control valve 9, 10 or gases flow generators 20, 21 acts in response to controller 1 action. This control action is based on the sensed airflow measurement from within each air channel and is based on achieving the desired inter-nasal airflow partitioning.

Differing air pressures are experienced at each naris to achieve a bias in inter-nasal airflow between each airway. This results in one airway experiencing airflow conditions that mimic it being actively being 'forced patent' and the other 'forced congested' throughout the whole breath cycle. This pressure offset experienced at each naris switches between airways during change in breath phases.

During inhalation, the 'forced patent' airway receives a greater air inflow from the air supply, causing its pressure to rise. On the other hand, the 'forced congested' airway receives a lower air inflow from the gases supply and hence achieves a lower pressure than the other airway. This difference in mask pressure during inhalation causes a greater air in-flow to occur at the naris of the 'forced patent' airway compared to that of the 'forced congested' airway.

During exhalation, the airflow into the nasal mask of the 'forced patent' side is reduced by the controller, enabling the pressure to remains fairly stable and at near air supply pressure level. Conversely, the 'forced congested' airway experiences an increase in gases inflow and hence achieves a higher pressure than that of the other airway. This elevation in pressure opposes air out-flow from the 'forced congested' naris while the airflow from the 'forced patent' naris experiences a lower opposing pressure force and hence less opposition to outflow. This swing in pressure between naris during exhalation maintains the desired airflow bias between each naris during this phase of the breath cycle.

Figure 19:
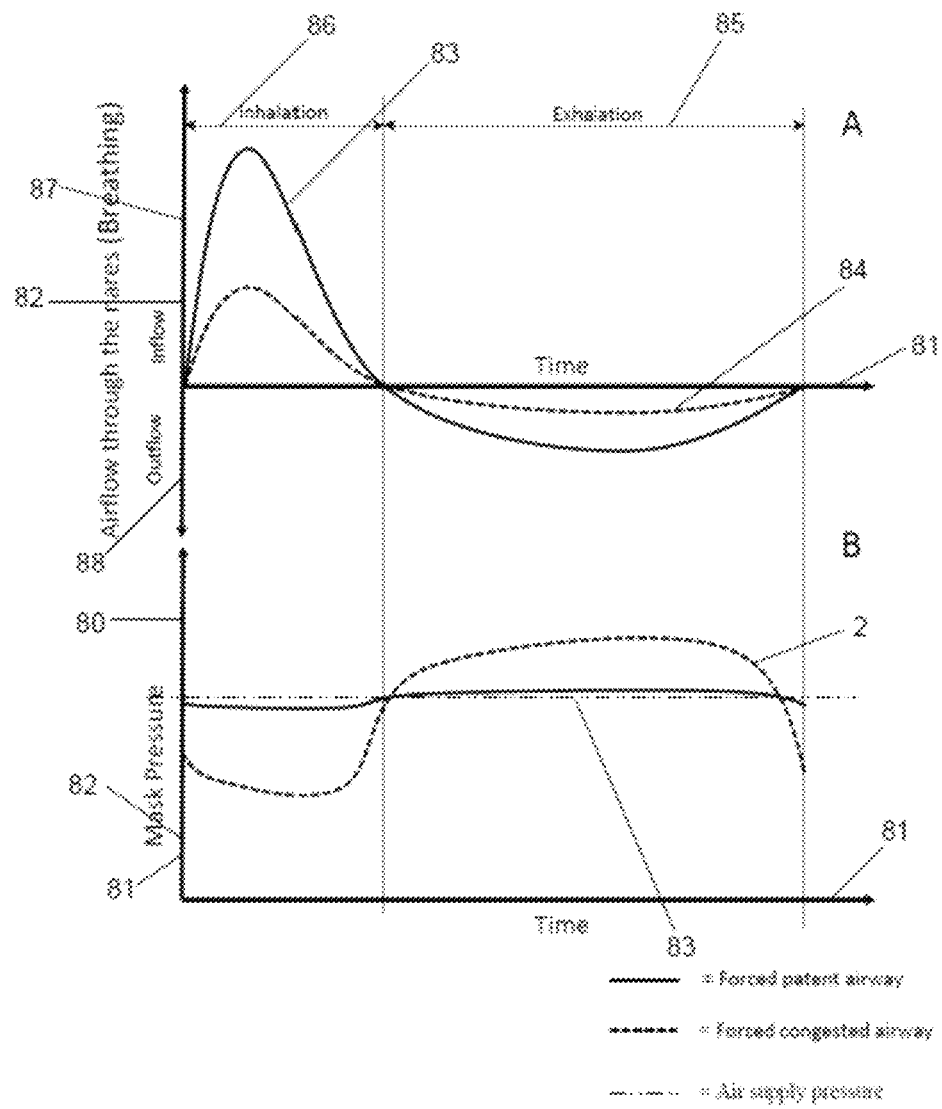
FIG. 19 shows a graph of the gases inflow and outflow during a single breath.

This inversion of pressure gradients experienced across the two airways during change in the phase of the breath cycle is essential to maintain the desired airflow bias between each of the nasal airways. The relationship between inter-nasal airflow partitioning and inter-nasal mask pressure over one breath cycle shown in FIG. 19.

Figure 20:
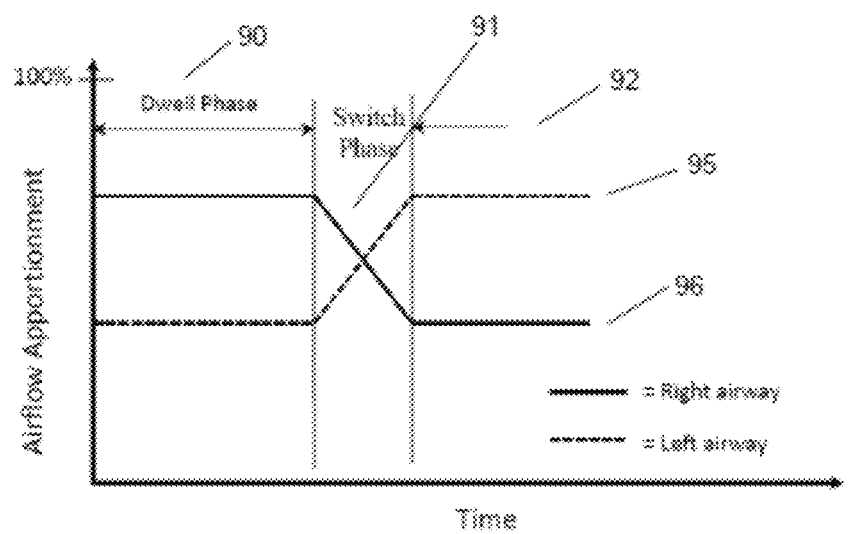
FIG. 20 shows a graph of the gases inflow and outflow during a breathing cycle.

Periodically the controller 1 will switch the bias as discussed above to optimise the user's experience. Change in the bias in airflows occurring between each naris, termed switching, mimics the physiological change in the nasal cycle. This is achieved by progressively exchanging the control set points between airways over a designated time interval. The result of change in this parameter in terms of inter-nasal airflow partitioning is demonstrated by FIG. 20 in the region labelled 'switch phase'.

While the present invention has been illustrated by the description of the embodiments thereof, and while the embodiments have been described in detail, it is not the intention of the Applicant to restrict or in any way limit the scope of the appended claims to such detail. Further, the above embodiments may be implemented individually, or may be combined where compatible. Additional advantages and modifications, including combinations of the above embodiments, will readily appear to those skilled in the art. Therefore, the invention in its broader aspects is not limited to the specific details, representative apparatus and methods, and illustrative examples shown and described. Accordingly, departures may be made from such details without departure from the spirit or scope of the Applicant's general inventive concept.

REFERENCES

1. Hanif, J., S. S. M. Jawad, and R. Eccles, The nasal cycle in health and disease. Clinical Otolaryngology, 2000. 25(6): p. 461-467.
2. Bartley, J., Breathing Matters: a New Zealand Guide. 1st. ed. 2006, Auckland: Random House. 219.
3. Elad, D., M. Wolf, and T. Keck, Air-conditioning in the human nasal cavity. Respiratory Physiology and Neurobiology, 2008. 163(1-3): p. 121-127.
4. Naftali, S., et al., The air-conditioning capacity of the human nose. Ann Biomed Eng, 2005. 33(4): p. 545-553.
5. Chhabra, N. and S. M. Houser, The Diagnosis and Management of Empty Nose Syndrome. Otolaryngologic Clinics of North America, 2009. 42(2): p. 311-330.
6. Drettner, B., B. Falck, and H. Simon, Measurements of the Air Conditioning Capacity of the Nose During Normal and Pathological Conditions and Pharmacological Influence. Acta Oto-Laryngologica, 1977. 84(1-6): p. 266-277.
7. Keck, T., et al., Humidity and temperature profile in the nasal cavity. Rhinology, 2000. 38(4): p. 167-171.

8. Cole, P., Modification of Inspired Air, in The Nose: Upper Airway Physiology and the Atmospheric Environment., D. F. Proctor and I. Andersen, Editors. 1982, Elsevier Biomedical Press: Amsterdam. p. 351-375.

9. Wolf, M., et al., Air-conditioning characteristics of the human nose. Journal of Laryngology and Otology, 2004. 118(2): p. 87-92.

10. Warren, N., E. Crampin, and M. Tawhai, The Role of Airway Epithelium in Replenishment of Evaporated Airway Surface Liquid From the Human Conducting Airways. Annals of Biomedical Engineering, 2010. 38(12): p. 3535-3549.

11. Eccles, R., Neurological and pharmacological considerations, in The nose: upper airway physiology and the atmospheric environment., D. F. Proctor and I. Andersen, Editors. 1982, Elsevier Biomedical Press: Amsterdam. p. 191-214.

12. White, D. E., J. Bartley, and R. Nates, Model demonstrates functional purpose of the nasal cycle. Biomedical Engineering Online, 2015. 14(38): p. 11.

13. Jella, S. A. and D. S. Shannahoff-khalsa, The effects of unilateral forced nostril breathing on cognitive performance. International Journal of Neuroscience, 1993. 73(1-2): p. 61-68.

14. Shannahoff-khalsa, D. S., M. R. Boyle, and M. E. Buebel, The Effects of Unilateral Forced Nostril Breathing on Cognition. International Journal of Neuroscience, 1991. 57(3-4): p. 239-249.

15. Shannahoff-Khalsa, D. S., et al., Ultradian rhythms of alternating cerebral hemispheric EEG dominance are coupled to rapid eye movement and non-rapid eye movement stage 4 sleep in humans. Sleep Medicine, 2001. 2(4): p. 333-346.

16. Shannahoff-khalsa, D. S. and F. E. Yates, Ultradian Sleep Rhythms of Lateral EEG, Autonomic, and Cardiovascular Activity Are Coupled in Humans. International Journal of Neuroscience, 2000. 101(1-4): p. 21-43.

17. Shannahoff-Khalsa, D. S., et al., Low-frequency ultradian insulin rhythms are coupled to cardiovascular, autonomic, and neuroendocrine rhythms. American Journal of Physiology—Regulatory, Integrative and Comparative Physiology, 1997. 272(3): p. R962-R968.

18. Martins de Araujo, M. T., et al., Heated humidification or face mask to prevent upper airway dryness during continuous positive airway pressure therapy. Chest, 2000. 117: p. 142-147.

19. Massie, C. A., et al., Effects of humidification on nasal symptoms and compliance in sleep apnea patients using continuous positive airway pressure. Chest, 1999. 116: p. 403-408.

20. Neill, A. M., et al., Humidified nasal continuous positive airway pressure in obstructive sleep apnoea. European Respiratory Journal, 2003. 22(2): p. 258-262.

21. Rakotonanahary, D., et al., Predictive factors for the need for additional humidification during nasal continuous positive airway pressure therapy. Chest, 2001. 119(2): p. 460-465.

22. Wiest, G. H., et al., A heated humidifier reduces upper airway dryness during continuous positive airway pressure therapy. Respiratory Medicine, 1999. 93(1): p. 21-26.

23. Worsnop, C. J., S. Miseski, and P. D. Rochford The routine use of humidification with nasal continuous positive airway pressure. Internal Medicine Journal, 2009. 99, DOI: 10.1111/j.1445-5994.2009.01969.x.

24. Dolan, D. C., et al., Longitudinal comparison study of pressure relief (C-Flex™) vs. CPAP in OSA patients. Sleep and Breathing, 2009. 13(1): p. 73-7.

25. Arfoosh, R. and J. Rowley, Continuous positive airway pressure for obstructive sleep apnea: an update. Journal of Respiratory Diseases, 2008. 29(9): p. 365-373.

26. Mador, M. J., et al., Effect of heated humidification on compliance and quality of life in patients with sleep apnea using nasal continuous positive airway pressure. Chest, 2005. 128(4): p. 2151-2158.

27. Goldstein, L., N. W. Stoltzfus, and J. F. Gardocki, Changes in interhemispheric amplitude relationships in the EEG during sleep. Physiology & Behavior, 1972. 8(5): p. 811-815.

28. Kimura, A., et al., Phase of nasal cycle during sleep tends to be associated with sleep stage. The Laryngoscope, 2013.

The invention claimed is:

1. A method of controlled delivery of breathing gases, comprising:
  during a first mode where a first naris of a patient is a patent naris that passes a majority of airflow and a second naris of the patient is a congested naris that passes less airflow than the patent naris:
    applying breathing gas pressure within the first naris of the patient during inhalation;
    applying breathing gas pressure within the second naris of the patient during inhalation;
    applying breathing gas pressure within the first naris of the patient during exhalation; and
    applying breathing gas pressure within the second naris of the patient during exhalation,
    wherein the breathing gas pressure applied to the first naris during inhalation is higher than the breathing gas pressure applied to the second naris during inhalation and the breathing gas inflow to the patient is predominantly through the first naris during inhalation, and wherein the breathing gas pressure applied to the first naris during exhalation is lower than the breathing gas pressure applied to the second naris during exhalation and the gas outflow from the patient is predominantly through the first naris during exhalation.

2. The method of controlled delivery of gases as claimed in claim 1 wherein the method forces the breathing gases inflow and outflow through the first naris.

3. The method of controlled delivery of gases as claimed in claim 1 wherein the pressure differences between each nares are greater at the midpoint of the inhalation and exhalation phases than they are at the start and end of each phase.

4. The method of controlled delivery of gases as claimed in claim 1 wherein the largest pressure differences between each nares are applied when net patient air flow, in or out, is above a certain threshold.

5. The method of controlled delivery of gases as claimed in claim 1 wherein the pressure differences are the smallest during the start and end of the inhalation and exhalation phases.

6. The method of controlled delivery of gases as claimed in claim 1 wherein the pressure delivered to one naris always achieves the maximal titration pressure during peak airflow for either inhalation or exhalation phases.

7. The method of controlled delivery of gases as claimed in claim 1 wherein the lower pressure is progressively elevated to the maximal titration pressure commencing at the start and end of the inhalation and start and end of the exhalation phase.

8. The method of controlled delivery of gases as claimed in claim 1 wherein the lower pressure is progressively elevated to the higher pressure when at least one of the flow rates is below a certain threshold and/or when the rate of change of at least one of the flow rates is below a certain threshold.

9. The method of controlled delivery of gases as claimed in claim 1 wherein the maximal titration pressure is set by one of the group consisting of a continuous set value, a pre-set bi-level value, measured airflow and a pre-determined pressure relief function.

10. The method of controlled delivery of gases as claimed in claim 1 wherein the method is used for one or more of the group consisting of treating snoring, treating obstructive sleep apnoea and oxygen therapy.

11. The method for controlled delivery of gases as claimed in claim 1 wherein the breathing gas flow to and from the patient is predominantly through a naris when the naris conducts between 55% and 80% of the breathing gas flow.

12. The method of controlled delivery of gases as claimed in claim 1 wherein during a second mode pressures are switched to control the breathing gas inflow and outflow substantially through the second naris after a period of time greater than one breath cycle, and wherein during the second mode the second naris is the patent naris that passes a majority of airflow and the first naris is the congested naris that passes less airflow than the patent naris.

13. The method of controlled delivery of breathing gases as claimed in claim 12, wherein the change in the pressures applied to the first and second naris is driven by a predetermined period that is user programmable, wherein the predetermined period is 5 minutes to 360 minutes.

14. An apparatus for the controlled delivery of breathing gases to a patient, comprising:
  a fluid connection between a gases flow generator and each of a first and second naris of the patent; and
  a controller for controlling the pressure of the gases supplied to the first and second naris of the patent, the controller configured to automatically:
    during a first mode where the first naris is a patent naris that passes a majority of airflow and the second naris is a congested naris that passes less airflow than the forced patent naris:
      apply breathing gas pressure within the first naris of a patient during inhalation;
      apply breathing gas pressure within the second naris of the patient during inhalation;
      apply breathing gas pressure within the first naris of the patient during exhalation; and
      apply breathing gas pressure within the second naris of the patient during exhalation,
    wherein the breathing gas pressure applied to the first naris is higher than the breathing gas pressure applied to the second naris during inhalation such that the breathing gas inflow to the patient is predominantly through the first naris, and wherein the breathing gas pressure applied to the first naris is lower than the breathing gas pressure applied to the second naris during exhalation such that the gas outflow from the patient is predominantly through the first naris.

15. The apparatus for the controlled delivery of a breathing gas to a patient as claimed in claim 14 wherein the controller forces the breathing gases inflow and outflow through the first naris.

16. The apparatus for the controlled delivery of a breathing gas to a patient as claimed in claim 14 wherein the apparatus is used for one or more of the group consisting of treating snoring, treating obstructive sleep apnoea and oxygen therapy.

17. The apparatus for the controlled delivery of a breathing gas to a patient as claimed in claim 14 wherein the gases flow generator comprises at least two gases flow generators and wherein at least two of the at least two gases flow generators are separately controllable.

18. The apparatus for the controlled delivery of a breathing gas to a patient as claimed in claim 14 wherein the breathing gas flow to and from the patient is predominantly through a naris when the naris conducts between 55% and 80% of the breathing gas flow.

19. The apparatus for the controlled delivery of a breathing gas to a patient as claimed in claim 14 wherein the controller periodically changes the pressures applied to the first and second naris during a second mode where the second naris is the patent naris that passes a majority of airflow and the first naris is the congested naris that passes less airflow than the patent naris, wherein during the second mode the breathing gas pressure applied to the first naris is lower than the breathing gas pressure applied to the second naris during inhalation such that the breathing gas inflow to the patient is substantially through the second naris, and wherein during the second mode the breathing gas pressure applied to the first naris is higher than the breathing gas pressure applied to the second naris during exhalation such that the gas outflow from the patient is substantially through the second naris.

20. The apparatus for the controlled delivery of a breathing gas to a patient as claimed in claim 19 wherein the change in the pressures applied to the first and second naris is driven by a predetermined period that is user programmable, wherein the predetermined period is 5 minutes to 360 minutes.

21. A method of controlled delivery of breathing gases, comprising:
  during a first mode:
    applying breathing gas pressure within a first naris of a patient during inhalation;
    applying breathing gas pressure within a second naris of the patient during inhalation, wherein the breathing gas pressure applied to the first naris during inhalation is higher than the breathing gas pressure applied to the second naris during inhalation and the breathing gas inflow to the patient is predominantly through the first naris during inhalation;
    applying breathing gas pressure within the first naris of the patient during exhalation; and
    applying breathing gas pressure within the second naris of the patient during exhalation, wherein the breathing gas pressure applied to the first naris during exhalation is lower than the breathing gas pressure applied to the second naris during exhalation and the gas outflow from the patient is predominantly through the first naris during exhalation; and
  during a second mode that occurs after the first mode:
    applying breathing gas pressure within the first naris of the patient during inhalation;
    applying breathing gas pressure within the second naris of the patient during inhalation, wherein the breathing gas pressure applied to the second naris during inhalation is higher than the breathing gas pressure applied to the first naris during inhalation and the breathing gas inflow to the patient is predominantly through the second naris during inhalation;
    applying breathing gas pressure within the first naris of the patient during exhalation; and
    applying breathing gas pressure within the second naris of the patient during exhalation, wherein the breathing gas pressure applied to the second naris during exhalation is lower than the breathing gas pressure applied to the first naris during exhalation and the gas outflow from the patient is predominantly through the second naris during exhalation.

22. The method of controlled delivery of breathing gases as claimed in claim 21 wherein switching from the first mode to the second mode is driven by a predetermined period that is user programmable, and wherein the predetermined period is 5 minutes to 360 minutes.

23. The method of controlled delivery of breathing gases as claimed in claim 21 wherein switching from the first mode to the second mode occurs driven by after a period of time greater than one breath cycle.

24. The method of controlled delivery of breathing gases as claimed in claim 21 wherein during the first mode the first naris is a patent naris that passes a majority of airflow and the second naris is a congested naris that passes less airflow than the patent naris, and wherein during the second mode the second naris is the patent naris that passes a majority of airflow and the first naris is the congested naris that passes less airflow than the patent naris.

25. The method of controlled delivery of breathing gases as claimed in claim 24 wherein the patent naris is a forced patent naris that is forced to conduct a majority of airflow and the congested naris is a forced congested naris that is forced to conduct less airflow than the forced patent naris.

* * * * *